(12) United States Patent
Huang et al.

(10) Patent No.: US 10,550,095 B2
(45) Date of Patent: Feb. 4, 2020

(54) CANCEROUS CELL GROWTH INHIBITING COMPOUNDS

(71) Applicant: WISYS TECHNOLOGY FOUNDATION, INC., Madison, WI (US)

(72) Inventors: Cheng-Chen Huang, Prescott, WI (US); Aaron P. Monte, La Crosse, WI (US)

(73) Assignee: WISYS TECHNOLOGY FOUNDATION, INC., Madison, WI (US)

( * ) Notice: Subject to any disclaimer, the term of this patent is extended or adjusted under 35 U.S.C. 154(b) by 0 days.

(21) Appl. No.: 15/482,302

(22) Filed: Apr. 7, 2017

(65) Prior Publication Data

US 2017/0342047 A1 Nov. 30, 2017

Related U.S. Application Data

(60) Provisional application No. 62/319,616, filed on Apr. 7, 2016.

(51) Int. Cl.

| | |
|---|---|
| *C07D 333/56* | (2006.01) |
| *C07C 43/23* | (2006.01) |
| *C07C 323/18* | (2006.01) |
| *C07D 333/16* | (2006.01) |
| *C07D 231/12* | (2006.01) |
| *C07D 209/12* | (2006.01) |
| *C07D 231/56* | (2006.01) |
| *C07D 241/18* | (2006.01) |
| *C07C 323/20* | (2006.01) |

(52) U.S. Cl.
CPC ............ *C07D 333/56* (2013.01); *C07C 43/23* (2013.01); *C07C 323/18* (2013.01); *C07C 323/20* (2013.01); *C07D 209/12* (2013.01); *C07D 231/12* (2013.01); *C07D 231/56* (2013.01); *C07D 241/18* (2013.01); *C07D 333/16* (2013.01)

(58) Field of Classification Search
None
See application file for complete search history.

(56) References Cited

U.S. PATENT DOCUMENTS 8,530,512 B2 * 9/2013 Monte .................. A61K 31/085
514/438

OTHER PUBLICATIONS

Yang et al., Bioorganic & Medicinal Chemistry Letters (2002), 12(7), pp. 1013-1015.*
Asianscientist: http://www.asianscientist.com/features/skin-whitening-products-asia-2012/.
Choi et al., "Zebrafish as a new model for phenotype-based screening for melanogenic regulatory compounds", Pigment Cet Res. 20; 120-127, 2007.
Kanebo (2013): http://www.kanebo.com/pressroom/pressrelease/20130723.pdf.
Kabir et al., "New class of gram-positive antibacterials: Inhibitors of MRSA and surrogates of the causative agents of anthrax and tuberculosis", Bioorg. Med. Chem. Lett. 18: 5745-5749, 2008.
Rodriguez et al., "Reversibie neuronal and muscular toxicity of caffeine in developing vertebrates", Comp. Biochem. Physiol. Part C (in press); 2014.
Smit, et al., "The hunt for natural skin whitening agents", Int. J. Mol. Sci. 10:5326-4349, 2009.
Langer, "New Methods of Drug Delivery", Science, 249: 1527-71533, Sep. 28, 1990.
Sefton et al., "Microencapsulation of Mammalian Cells in a Water-Insoluble Polyacrylate by Coextrusion and Interfacial Precipitation", Biotechnology and Bioengineering, vol. XXIX, pp. 1335-1143, 1987.
Buchwal et al., Surgery 88:507 (1980).
Saudek et al., N. Engl. J. Med. 321:574 (1989).
Goodson, Medical Applications of Controlled Release, supra, vol. 2, pp. 115-138 (1984).
Seidel et al., "Anisotropic Etching of Crystalline Silicon in Alkaline Solutions", J. Electrochem. Soc., vol. 137, No. 11, Nov. 1990.
"Liposomes in the Therapy of Infectious Disease and Cancer", Lopez-Beresten and Fidler (eds.), Liss, NY, pp. 245-262 (1989).
Davis et al., "Alteration of the circulating life and antigenic properties of bovine adenosine deaminase in mice by attachment of polyethylene glycol", Clin. Exp. Immunol. (1981) 46, 649-652.
Katre et al., "Chemical modification of recombinant interleukin 2 by polyethylene glycol increases its potency in the murine Meth A sarcoma model", Proc. Natl. Acad. Sci., vol. 84, pp. 1487-1491, Mar. 1987.

* cited by examiner

*Primary Examiner* — Brian J Davis
(74) *Attorney, Agent, or Firm* — Boyle Fredrickson, S.C.

(57) ABSTRACT

The present invention provides a compound of Formula I, II or III or a salt or prodrug or derivative thereof that is useful for skin-whitening by inhibiting melanin formation and removing existing melanin and the inhibition of melanoma growth and/or the removal of existing melanoma cells.

2 Claims, 17 Drawing Sheets

CANCEROUS CELL GROWTH INHIBITING COMPOUNDS

CROSS-REFERENCE TO RELATED APPLICATIONS

This application claims priority from U.S. Provisional Application Ser. No. 62/319,616, filed on Apr. 7, 2016, the entirety of which is expressly incorporated herein by reference.

FIELD OF THE INVENTION

The present invention relates generally to compounds for affecting the skin, and more specifically to compounds for lightening the pigment of skin and/or inhibiting cancerous cell growth.

BACKGROUND OF THE INVENTION

Skin whitening has been a major practice in the cosmetic industry. It interests many due to the ability to correct uneven skin pigment, treat pigmentation disorders, such as melasma, and provide an avenue to lighten natural skin pigmentation, which is thought to be aesthetically pleasing in a variety of cultures. For instance, in Asia the fastest growing markets include skin-whitening as it brings in billions of dollars annually. Current treatment options include chemicals (Smit et al., 2009), laser, and cryosurgery. While chemicals often are the simplest and most affordable treatment option, many chemicals are found to have adverse health effects including skin sensitivity, and cancers such as leukemia. For example, hydroquinone is a strong inhibitor of melanin (black pigment) production but was banned in Europe because of its link to leukemia and other cancer risks. Arbutin is a natural source of hydroquinone present in the leaf extracts of many kinds of berries. However, although natural, the safety of arbutin has not been well documented and the supply of arbutin is limited. Tretinoin, another proven effective skin whitener, conversely may lead to darkened skin pigmentation after time, and increases skin sensitivity to UVA and UVB rays. Other substitutes such as azelaic acid and vitamin C have limited whitening abilities and the effects diminish after a period of time.

One of the attributes of melanin is its production in melanocytes, which also form the cells that can become cancerous melanoma upon exposure to UV rays. Thus, it is beneficial to inhibit the growth of melanocytes, such as by using a skin-whitening compound that affects melanocytes, to slow or stop the proliferation of melanomas produced from melanocyte cells.

Thus, it is desirable to develop new skin whitening chemicals that act in different mechanistic pathways than the present therapeutic options in hopes of developing safer skin-whitening and melanin/melanoma treatment alternatives.

SUMMARY OF THE INVENTION

According to one aspect of the present invention, the present invention provides a compound of Formula I, II or III or a salt or prodrug or derivatives thereof, including but not limited to ether derivatives, acid derivatives, amide derivatives, ester derivatives and the like. Generally, the compound, salt or prodrug is a skin-whitening agent useful for the inhibition of melanin synthesis and/or the removal of existing melanin to function as a skin-whitening agent.

According to another aspect of the disclosure, this project presents our discovery of a family of compounds, such as those compounds of Formula I, II or III or a salt or prodrug or derivatives thereof, that showed high potency in inhibiting pigment formation and no detectable toxicity. More interestingly, our compounds inhibit melanoma growth. Molecular characterizations suggest that our compounds have novel mechanisms for pigment inhibition and melanoma inhibition than other known compounds. These results suggest that our compounds could be a safer skin-whitening reagent and a new melanoma therapeutic drug.

According to an exemplary embodiment of the present invention, the present invention provides skin whitening compound of Formula I, or a salt or prodrug or derivatives thereof, including but not limited to ether derivatives, acid derivatives, amide derivatives, ester derivatives and the like, useful for inhibiting melanin synthesis and removal of existing melanin pigmentation. Formula I is shown as follows:

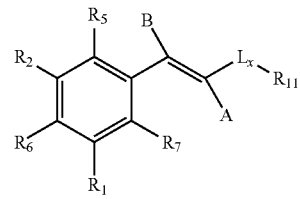

wherein:
$R_1$ is not H when $R_2$ is H and $R_2$ is not H when $R_1$ is H, further wherein $R_1$ is $CH_{(2n+1)}O$, wherein n is 1-10;
$R_2$ is OH or $CH_{(2n+1)}O$, wherein n is 1-10;
A, B and $R_1$, $R_2$, $R_5$, $R_6$, and $R_7$ are separately and independently selected from a group consisting of H, alkyl and aryl groups;
$R_{11}$ is an alkyl or an aryl group; and
L is an optional linker or linking group, with x=0 or 1, i.e., if x=0, no linking group is present.

As is noted, "L" is an optional linking group. Various suitable linking groups will be suggested to one skilled in this art in view of this disclosure. "L" is preferably a chalcogen, more preferably O, or S. "L" can also be, essentially, a divalent linking structure known to the art. For example, "L" can be —$CH_2$—, lower alkyl, amino e.g., —NH—, —NR— where R is lower alkyl, and —$CF_2$— among many others.

According to another exemplary embodiment of the present invention, the skin whitening compound, salt or prodrug or derivatives thereof, including but not limited to ether derivatives, acid derivatives, amide derivatives, ester derivatives and the like, is according to Formula II:

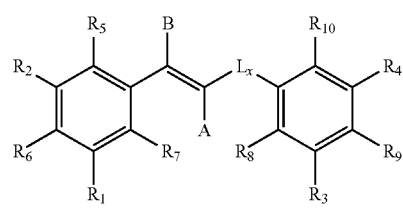

Formula (II)

wherein:
$R_1$ is not H when $R_2$ is H and $R_2$ is not H when $R_1$ is H, further wherein $R_1$ is $CH_{(2n+1)}O$, wherein n is 1-10;

$R_2$ is OH or $CH_{(2n+1)}O$, where n is 1-10;

A, B and $R_3$ through $R_{10}$ are separately and independently selected from a group consisting of H, alkyl and aryl groups; and L is an optional linker or divalent linking group, with x=0 or 1, i.e., if x=0, no linking group is present.

In a preferred embodiment, $R_1$ is $CH_3O$, $R_2$ is OH or $CH_{(2n+1)}O$, where n is 1-10; and A, B and $R_3$ through $R_{10}$ are independently selected from a group consisting of H, alkyl and aryl groups.

In another preferred embodiment, $R_1$ is $CH_3O$, $R_2$ is OH and A, B and $R_3$ through $R_{10}$ are independently selected from a group consisting of H, alkyl and aryl groups.

In another exemplary aspect of the present invention the skin whitening compound, salt or prodrug or derivatives thereof, including but not limited to ether derivatives, acid derivatives, amide derivatives, ester derivatives and the like, is according to Formula III:

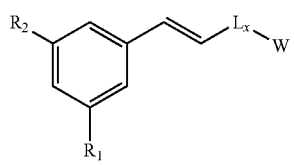

Formula III wherein:
$R_1$ is not H when $R_2$ is H and $R_2$ is not H when $R_1$ is H, further wherein $R_1$ is OH or $CH_{(2n+1)}O$, wherein n is 1-10;

$R_2$ is OH or $CH_{(2n+1)}O$, where n is 1-10;

W is alkyl, phenyl, halophenyl, pyridyl, piperidyl, or a substituted or unsubstituted aryl group, including certain unsubstituted and substituted aromatic heterocycles; and L is a linker or linking group selected from O, S, NH, $CF_2$, or $CH_2$, and x=0 or 1, i.e., if x=0, no linking group is present. The term "aryl" herein is to be broadly understood as is described below.

Yet another aspect of the present invention describes a method of whitening the skin in a subject in need thereof, said method comprising the step of administering an effective amount of a compound having a structure represented by Formulas I, II or III or a salt or prodrug, derivatives thereof, including but not limited to ether derivatives, acid derivatives, amide derivatives, ester derivatives and the like, thereof.

Another aspect of the invention provides a pharmaceutical composition, comprising: (a) an effective amount of a compound having a chemical structure represented by Formula I, II or III, or a salt or a prodrug or derivative thereof, including but not limited to ether derivatives, acid derivatives, amide derivatives, ester derivatives and the like; and (b) a pharmaceutically-acceptable carrier. The compound, salt or prodrug, or derivative is a skin-whitening agent.

Yet another aspect of the invention provides a method of inhibiting melanin synthesis and/or removing existing pigment in the skin. The method comprising contacting the skin in which melanin synthesis is to be inhibited or pigment removed with a melanin inhibiting or pigment removing amount of a compound according to Formula I, II or III, or, salt or prodrug or derivative thereof, including but not limited to ether derivatives, acid derivatives, amide derivatives, ester derivatives and the like.

Another aspect of the invention provides a composition suitable for inhibiting melanin synthesis and/or removing existing melanin in the skin. The composition comprises: a first ingredient which inhibits melanin synthesis and/or removes existing melanin in the skin comprising the compound, prodrug or salt or derivative thereof, including but not limited to ether derivatives, acid derivatives, amide derivatives, ester derivatives and the like of claim 1; and a second ingredient which comprises an acceptable carrier or an article of manufacture. In one embodiment, the acceptable carrier is a pharmaceutically acceptable carrier, an antibacterial agent, a skin conditioning agent, a lubricating agent, a coloring agent, a moisturizing agent, binding and anti-cracking agent, a perfuming agent, a brightening agent, a UV absorbing agent, a whitening agent, a transparency imparting agent, a thixotropic agent, a solubilizing agent, an abrasive agent, an antioxidant, a skin healing agent, a cream, a lotion, an ointment, a shampoo, an emollient, a patch a gel or a sol. In another embodiment, the article of manufacture is a textile, a fiber, a glove or a mask.

In yet another exemplary embodiment of the invention, the compound according to Formula I, II or III, or salt or prodrug or derivative thereof, including but not limited to ether derivatives, acid derivatives, amide derivatives, ester derivatives and the like is effective in inhibiting the growth of cancerous cells and/or killing existing cells, such as by inhibiting the growth or proliferation of melanocytes cells or cancerous melanoma cells, rendering the compounds an effective cancer treatment and/or chemotherapeutic agent.

Numerous other aspects, features, and advantages of the present invention will be made apparent from the following detailed description together with the drawings figures.

BRIEF DESCRIPTION OF THE DRAWINGS

The drawings illustrate the best mode currently contemplated of practicing the present invention.

In the drawings.

DETAILED DESCRIPTION OF THE INVENTION

Figure 1:
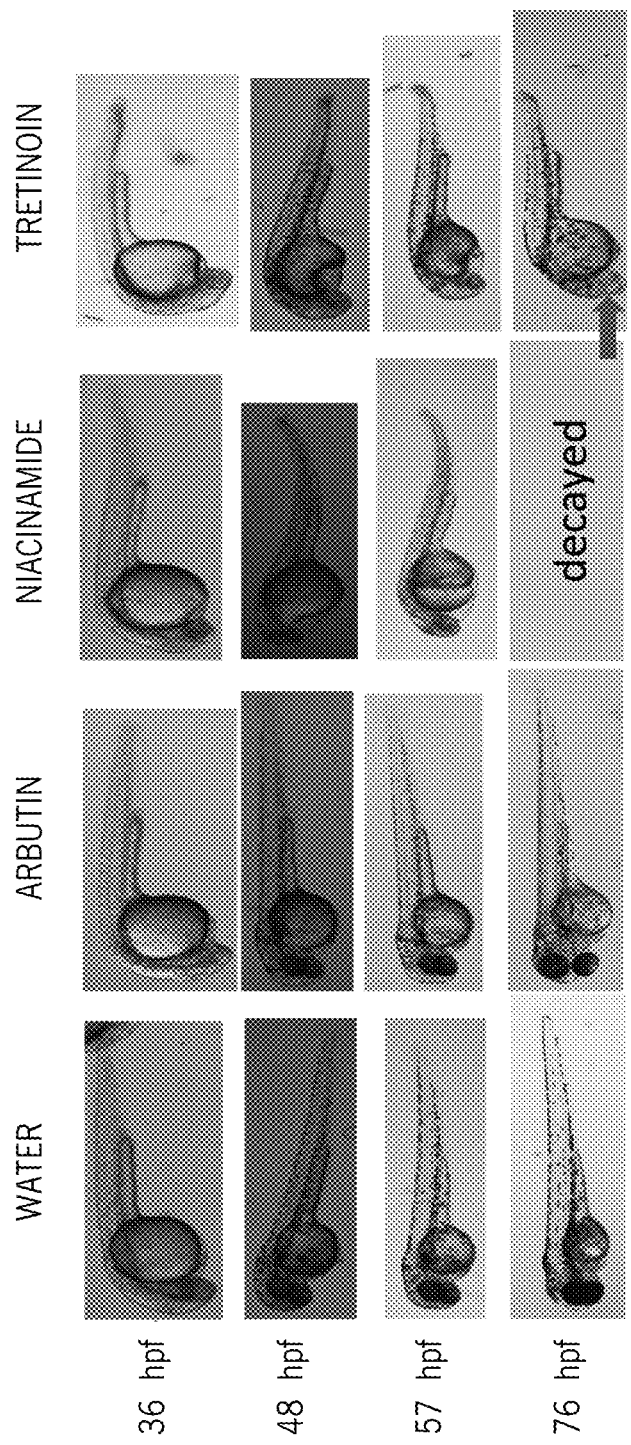
FIG. 1 are photo illustrations of the time-course progression of pigmentation inhibition in all embryos with exemplary embodiments of the human drug treatments of the present invention from 24-76 hpf in comparison to the water treated control group.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a compound" includes a plurality of such compounds and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to stereoisomers and analogs, structural isomers and analogs, conformational isomers and analogs, and the like. In one embodiment, this invention encompasses the use of different stereoisomers of skin whitening compound(s) of Formula I, II or III. It will be appreciated by those skilled in the art that the skin whitening compound(s) useful in the present invention may contain a chiral center. Accordingly, the compounds used in the methods of the present invention may exist in, and be isolated in, optically-active or racemic forms. Some compounds may also exhibit polymorphism. It is to be understood that the present invention encompasses the use of any racemic, optically-active, polymorphic, or stereoisomeric form, or mixtures thereof, which form possesses properties useful in the treatment of melanin and/or pigmentation conditions described and claimed herein. In one embodiment, the skin whitening compound(s) are the pure (Z) or (E)-isomers. In another embodiment, the skin whitening compound(s) are the pure (R) or (S)-isomers. In another embodiment, the compounds are a mixture of the (R) and the (S) isomers or (E) and (Z) isomers. In another embodiment, the compounds are a racemic mixture comprising an equal amount of the (R) and the (S) isomers. Furthermore, where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention. Preparation of these isomers, compounds and derivatives are well known to one of ordinary skill in the art.

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Pharmaceutically acceptable salts for topical administration to body surfaces using, for example, creams, gels, drops, and the like, include the skin whitening compound(s) or their physiologically tolerated derivatives such as salts, esters, N-oxides, and the like are prepared and applied as solutions, suspensions, or emulsions in a physiologically acceptable diluent with or without a pharmaceutical carrier.

This invention further includes methods utilizing derivatives of the skin whitening compound(s). The term "derivatives" includes but is not limited to ether derivatives, acid derivatives, amide derivatives, ester derivatives and the like. In addition, this invention further includes methods utilizing hydrates of the skin whitening compound(s). The term "hydrate" includes but is not limited to hemihydrate, monohydrate, dihydrate, trihydrate and the like.

This invention further includes methods of utilizing metabolites of the skin whitening compound(s). The term "metabolite" means any substance produced from another substance by metabolism or a metabolic process.

The present invention includes within its scope prodrugs of the skin whitening compound(s). In general, such prodrugs will be functional derivatives of the compound of Formula I which are readily convertible in vivo into the required compound of Formula I, II or III. Conventional procedures for the selection and preparation of suitable prodrug derivatives are described, for example, in Design of Prodrugs, ed, H. Bundgaard, Elsevier, 1985.

As defined herein, "contacting" means that the skin whitening compound(s) used in the present invention is introduced into a sample containing the receptor in a test tube, flask, tissue culture, chip, array, plate, microplate, capillary, or the like, and incubated at a temperature and time sufficient to permit binding of the skin whitening compounds to a receptor. Methods for contacting the samples with the skin whitening compounds or other specific binding components are known to those skilled in the art and may be selected depending on the type of assay protocol to be run. Incubation methods are also standard and are known to those skilled in the art.

In another embodiment, the term "contacting" means that the skin whitening compound(s) used in the present invention is introduced into a subject receiving treatment, and the compound is allowed to come in contact in vivo. In yet another embodiment, "contacting" includes topical application of the skin whitening compound(s) on a subject.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

In the treatment, the skin whitening compounds(s) may be administered in any suitable manner, such as on a regimen of 1 to 4 times per day, or on a continuous basis via, for example, the use of a transdermal patch.

As used herein, the term "administering" refers to bringing a patient, tissue, organ or cells in contact with skin whitening compounds according to Formulas I, II or III. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human or an animal, that: (1) has a melanin or pigmentation condition remediable or treatable by administration of the skin whitening compound(s) according to Formula I, II or III; or (2) is susceptible to a melanin or pigmentation condition that is preventable by administering the skin whitening compound(s) according to Formula I, II or III.

In yet another method according to the invention, a pharmaceutical composition can be administered in a controlled release system. For example, the agent may be delivered using intravenous infusion, an implantable osmotic pump, a transdermal patch, liposomes, or other modes of administration. In one embodiment, a pump may be used (see Langer, supra; Sefton, CRC Crit. Ref. Biomed, Eng. 14:201 (1987); Buchwald et al., Surgery 88:507 (1980); Saudek et al., N. Engl. J. Med. 321:574 (1989). In yet another embodiment, polymeric materials can be used. In yet another embodiment, a controlled release system can be placed in proximity to the therapeutic target, i.e., the skin, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, transdermally, intramuscularly, intravenously, intradermally, subcutaneously, intraperitoneally, intraventricularly, intracranially intrathecally, sublingually, rectally, vaginally, nasally, by inhalation, cutaneously, topically and systemically.

The pharmaceutical preparations administrable by the invention can be prepared by known dissolving, mixing, granulating, or tablet-forming processes. For oral administration, the anti-infective compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the anti-infective compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally of effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage from affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, "pharmaceutical composition" means therapeutically effective amounts of the skin whitening compound(s) together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of melanin or pigmentation development; and (b) the reversal or stabilization of melanin or pigmentation development. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

The liquid forms in which the pharmaceutical compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. Thus for example, in a preferred example, liquid form of the novel composition will include oral rinse solutions, anti-caries solutions, disinfectant solutions, and other liquids forms well known to one of ordinary skill in the art.

The preparation of pharmaceutical compositions which contain an active component is well understood in the art. Such compositions may be prepared as aerosols delivered to the nasopharynx or as injectable, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

Other embodiments of the compositions administered according to the invention incorporate particulate forms, protective coatings, protease inhibitors or permeation enhancers for various routes of administration, including parenteral, pulmonary, nasal and oral.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein ibid., pp. 317-327; see generally ibid).

The pharmaceutical preparation can comprise the skin whitening compound alone, or can further include a pharmaceutically acceptable carrier, and can be in solid or liquid form such as tablets, powders, capsules, pellets, solutions, suspensions elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the skin whitening compound can be administered to a subject by, for example, subcutaneous implantation of a pellet. In a further embodiment, a pellet provides for controlled release of a skin whitening compound over a period of time. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Pharmaceutically acceptable parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, anti-oxidants, collating agents, inert gases and the like.

Pharmaceutically acceptable carriers for controlled or sustained release compositions administrable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Pharmaceutically acceptable carriers include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; and Katre et al., 198). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Preferred Exemplary Embodiments

The inventors have found a compound that shows efficacy in skin whitening by inhibiting melanin synthesis and removal of existing melanin pigmentation in animals, such as fish and mammals, including humans, as well as a significant effect in removing and preventing proliferation of cancerous melanoma cells.

Accordingly, the present invention provides skin whitening/cancer treating compound of Formula I, or a salt or prodrug useful for inhibiting melanin synthesis and removal of existing melanin pigmentation. Formula I is shown as follows:

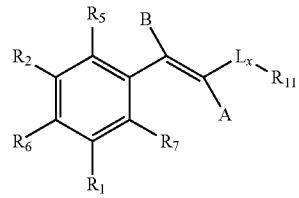

Formula I wherein:
$R_1$ is not H when $R_2$ is H and $R_2$ is not H when $R_1$ is H, further wherein $R_1$ is $CH_{(2n+1)}O$, wherein n is 1-10;
$R_2$ is OH or $CH_{(2n+1)}O$, wherein n is 1-10;
A, B and $R_1$, $R_2$, $R_5$, $R_6$, and $R_7$ are separately and independently selected from a group consisting of H, alkyl and aryl groups;
$R_{11}$ is an alkyl or an aryl group; and
L is an optional linker or linking group, with x=0 or 1, i.e., if x=0, no linking group is present.

As is noted, "L" is an optional linking group. Various suitable linking groups will be suggested to one skilled in this art in view of this disclosure. "L" is preferably a chalcogen, more preferably O, or S. "L" can also be, essentially, a divalent linking structure known to the art. For example, "L" can be lower alkyl, amino e.g., —NH—, —NR— where R is lower alkyl, and —CF$_2$— among many others.

In a preferred embodiment, the skin whitening/cancer treating compound, salt or prodrug is according to Formula II:

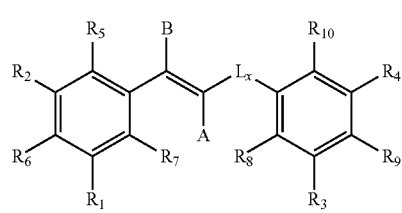

Formula (II)

wherein:
$R_1$ is not H when $R_2$ is H and $R_2$ is not H when $R_1$ is H, further wherein $R_1$ is $CH_{(2n+1)}O$, wherein n is 1-10;
$R_2$ is OH or $CH_{(2n+1)}O$, where n is 1-10;

A, B and $R_3$ through $R_{10}$ are separately and independently selected from a group consisting of H, alkyl and aryl groups; and L is an optional linker or divalent linking group, with x=0 or 1, i.e., if x=0, no linking group is present.

In a preferred embodiment, $R_1$ is $CH_3O$, $R_2$ is OH or $CH_{(2n+1)}O$, where n is 1-10; and A, B and $R_3$ through $R_{10}$ are independently selected from a group consisting of H, alkyl and aryl groups.

In another preferred embodiment, $R_1$ is $CH_3O$, $R_2$ is OH and A, B and $R_3$ through $R_{10}$ are independently selected from a group consisting of H, alkyl and aryl groups.

In another embodiment, said skin whitening/cancer treating compound, salt or prodrug is shown in Formula III as follows:

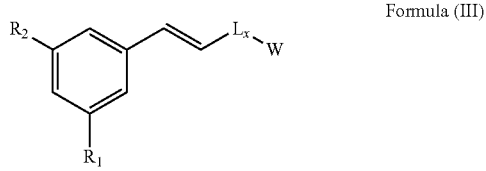

Formula (III)

or salt and prodrug thereof,
wherein:
$R_1$ is not H when $R_2$ is H and $R_2$ is not H when $R_1$ is H, further wherein $R_1$ is $CH_{(2n+1)}O$, wherein n is 1-10;
$R_2$ is OH or $CH_{(2n+1)}O$, where n is 1-10;
W is alkyl, phenyl, halophenyl, pyridyl, piperidyl, or a substituted or unsubstituted aryl group, including certain unsubstituted and substituted aromatic heterocycles.

Experimental

Three current human drugs, Arbutin, Niacinamide, and Tretinoin, and a known melanin synthesis inhibitor, phenylthiourea (PTU), were included as a comparison in various testing protocols in comparison with the melanin synthesis effects of certain exemplary compounds of the present invention, A11 and MEK-I, with MEK-I having the following structure:

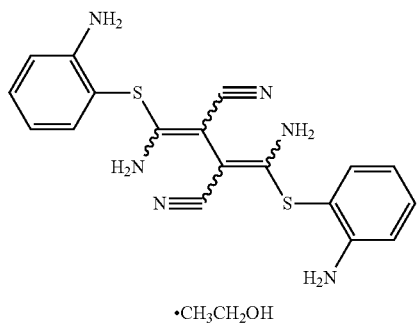 [SMILES: N#CC(=C(N)Sc1ccccc1N)C(C#N)=C(N)Sc1ccccc1N ; "·CH3CH2OH"]

·$CH_3CH_2OH$

The testing protocols for these compounds are as follows:
a. To test the inhibition of melanin synthesis, the zebrafish embryos were treated with the drugs from 24 to 76 hours post-fertilization (hpf). The embryos were monitored and imaged throughout their development to track the development of melanin pigment relative to a control group to which water was administered (Protocol 1).

b. To test the effects of the drugs on existing melanin and/or melanocytes, the embryos were treated with the chemicals at 48 hpf, after pigment had developed. The embryos were again monitored and imaged throughout their development relative to a control group to which water was administered (Protocol 2).
c. Additionally, to test the ability of the pigment to recover after being treated with our drugs, all embryos were treated at 24 hpf with the chemicals until the 48 hpf or 64 hpf time period, then washed with water to remove the treatment. The embryos were again monitored and imaged throughout their development relative to a control group to which water was administered (Protocol 3).

Comparison of Skin-Whitening Compounds

The skin-whitening effect of several compounds using zebrafish embryo, including three compounds currently used in humans, namely, Arhutin, Niacinamide, Tretinoin, a known melanin synthesis inhibitor, phenylthiourea (PTU) and the two new compounds identified by our lab A11 and MEK-I was tested using Protocol 1. The black pigment (or melanin) is very easy to observe in zebrafish. In brief, adult zebrafish are taken to breed embryos. Morphologically normal embryos of 24 hours post fertilization (hpf) stage were selected for incubation in the drugs from 24 to 76 hours. During the incubation, the embryos are monitored and imaged (see FIGS. 1 and 3) to track the development of melanin. This experiment was repeated at least three times to obtain a reproducible result. To broaden the comparison with other skin-whitening products, this project can also test at least three other compounds, Kojic acid, Gallic acid and Haginin. The results obtained from these experiments inform us of the skin-whitening efficacy as well as mechanistic difference between these compounds. In the meantime, the whole organism context also allows us to examine the toxicological profile, if any, of these compounds.

Figure 2:
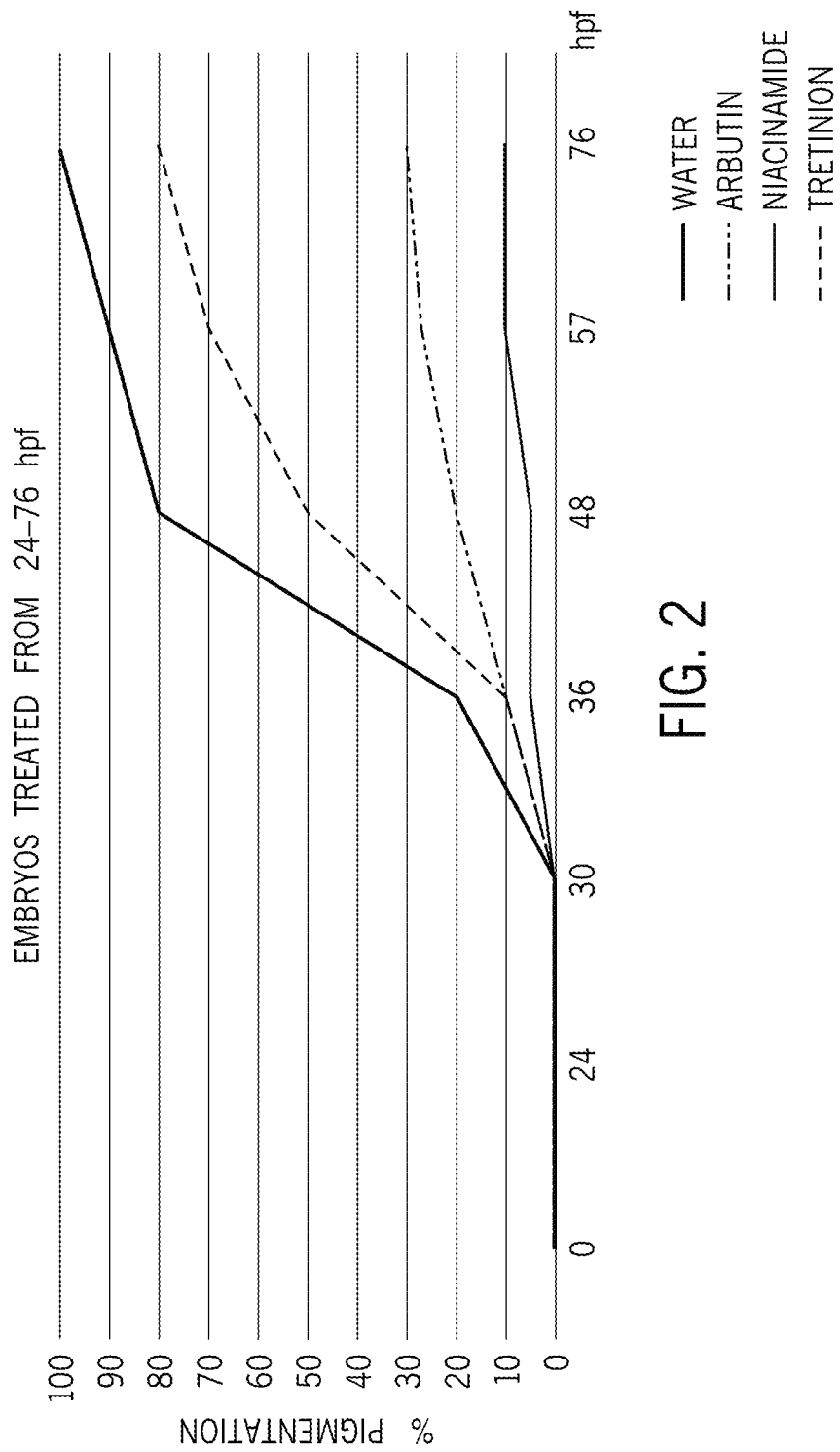
FIG. 2 is a graph of the quantification of the pigmentation in zebrafish embryos treated with exemplary embodiments of the human drugs of the present invention from 24 to 76 hpf showing that 100 µM Arbutin, 1% Niacinamide, and 0.1% Tretinoin reduce pigmentation to 30%, 10%, and 80% respectively in comparison to the control group.

In reference to FIGS. 1-2, the results show that:
The three human drugs work on zebrafish, as in humans.
The human drugs causes toxicity.

Figure 3:
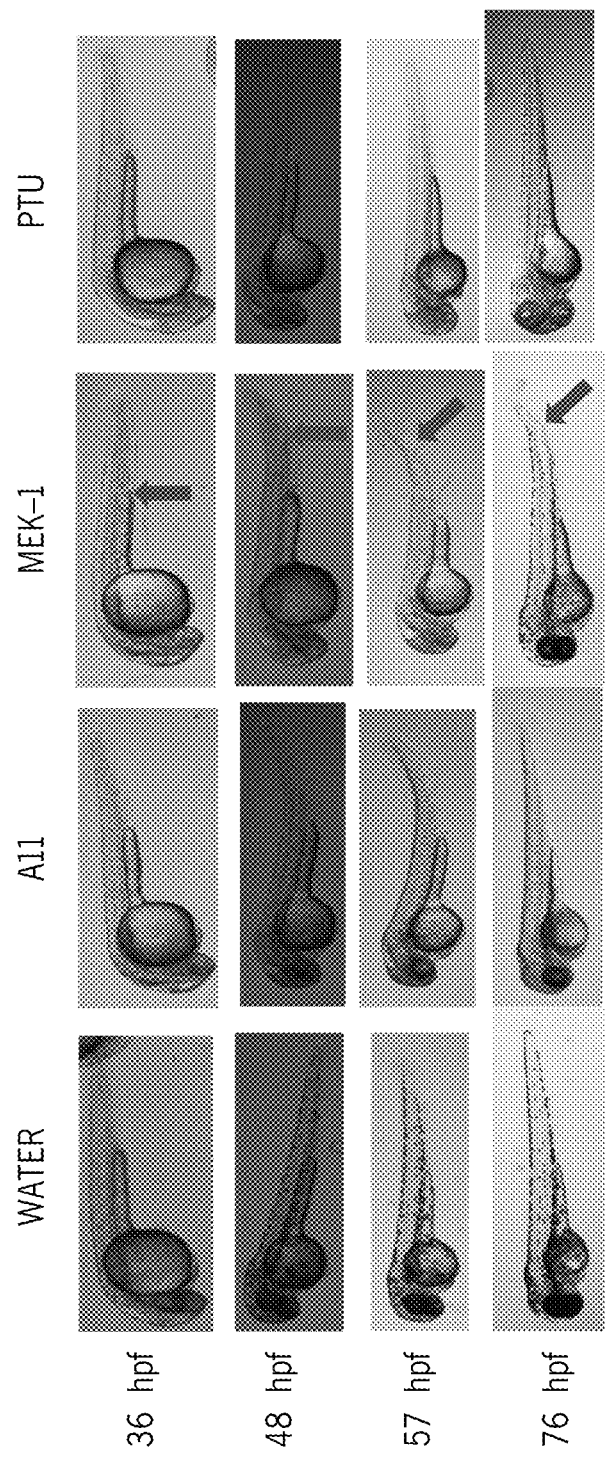
FIG. 3 are photo illustrations of the time course progression of pigmentation inhibition in all embryos treated with exemplary embodiments of the human drugs of the present invention from 2476 hpf, along with PTU. Both A11 and PTU result in nearly complete pigmentation loss. Notocord toxicity is present in MEK-I treated embryos (arrows)
Figure 4:
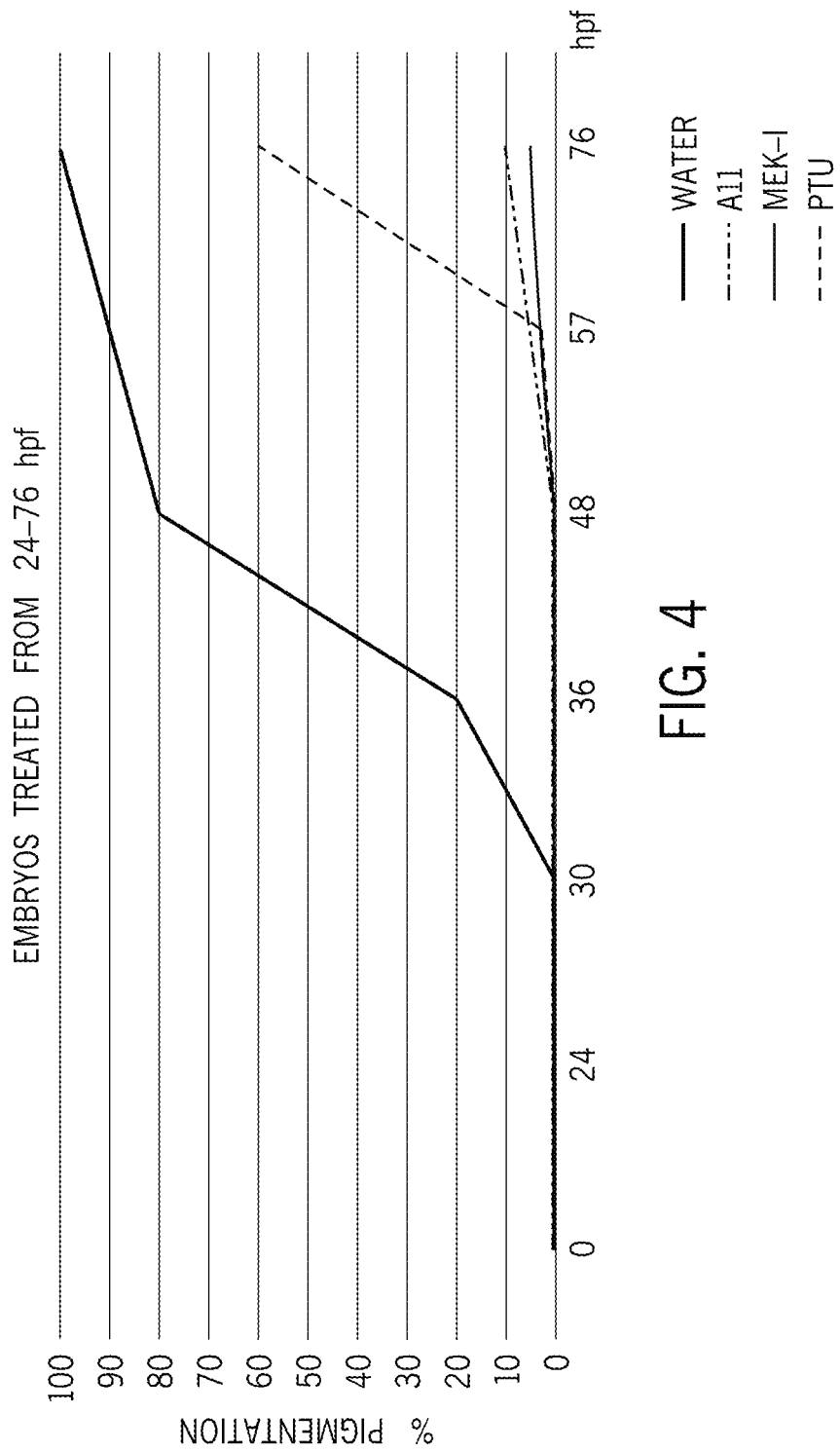
FIG. 4 is a graph of the quantification of the pigmentation in zebrafish embryos treated from 24-76 hpf shows that 10 µM A11 and 0.003% PTU reduce pigmentation almost entirely with percentages of <5 and 10% respectively. 10 µM MEK-I inhibits pigmentation to 60%.

In reference to FIGS. 3-4, the results show that:
The three drugs work on zebrafish, as in humans, with nearly complete pigmentation loss with PTU and A11.
MEK-I and PTU result in various levels of toxicity; while A11 does not.

The overall efficacy of the skin-whitening effects of the drugs tested according to the observed results is:
PTU>A11>Niacinamide>Arbutin>MEK-I>Tretinoin Testing the Skin-Whitening Efficacy on Existing Pigmentation To test the effects of the drugs on existing melanin and/or melanocytes, the embryos were treated with the chemicals A11, MEK-I and PTU at 48 hpf, after pigment had developed. The embryos were again monitored and imaged throughout their development according to Protocol 2.

Figure 5:
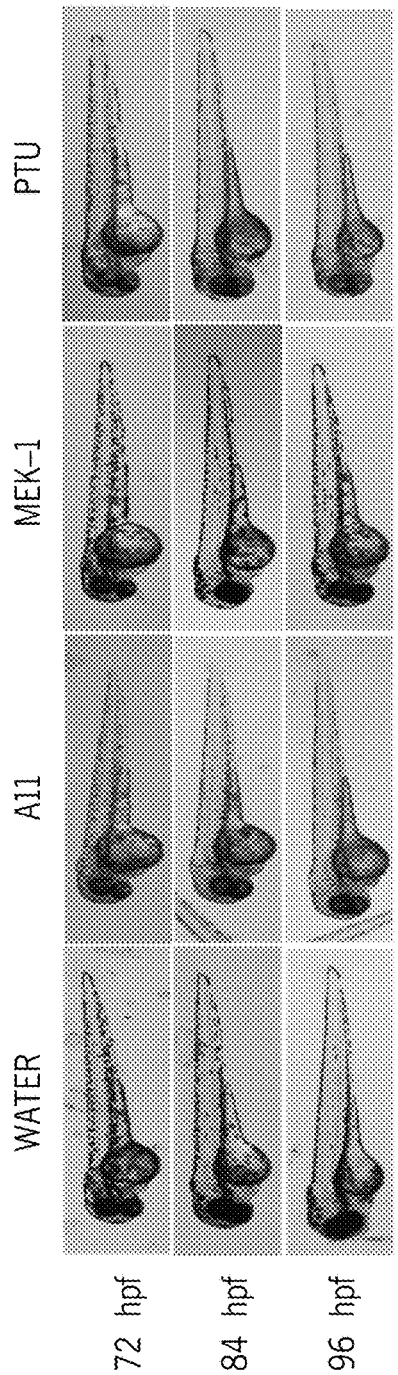
FIG. 5 are photo illustrations and a graph showing when the embryos are treated at 48 hpf, A11 and PTU reduce existing pigment to 20% by acting on existing melanin or melanocytes. However, the MEK-I treatment at 48 hpf is ineffective.
Figure 5:
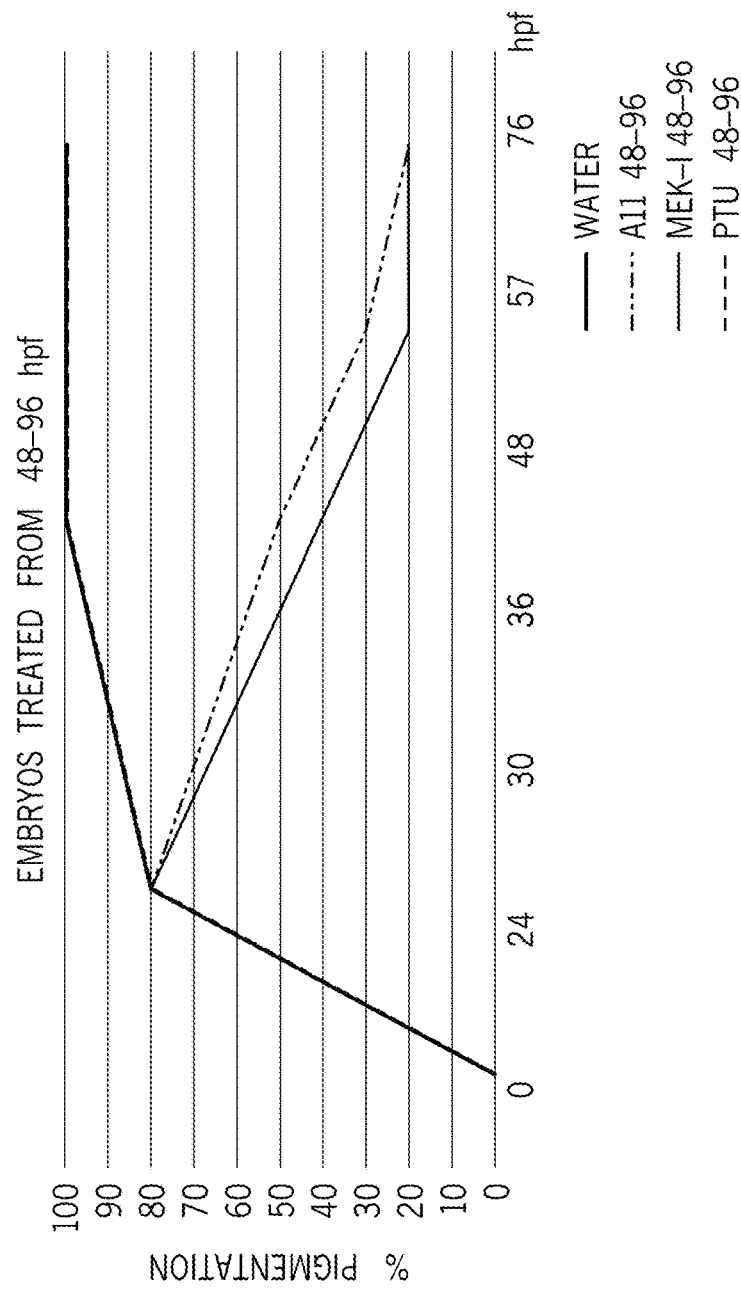

In reference to FIG. 5, the results show that:
PTU and A1 remove existing pigment; whereas, MEK-I has no effect, suggesting two different mechanistic pathways In addition, testing on the skin lightening efficiency of various compounds is shown in Table 1:

TABLE 1

Skin Lightening Efficacy of All Analogs on Zebrafish Embryos

| Analog | Pigmentation |
|--------|--------------|
| A1 | 80% |
| A3 | 80% |

TABLE 1-continued

Skin Lightening Efficacy of All Analogs on Zebrafish Embryos

| Analog | Pigmentation |
|---|---|
| A4 | 100% |
| A5 | 95% |
| A7 | 70% |
| A6, A10 | 50% |
| A8 | 10% |
| A9 | 10% |
| A11 | 10% |
| CL1 | 0% (40 uM) |
| CL2 | 5% |
| CL3 | 20% (40 uM) |
| CL4 | 0% |
| CL5 | 100% (40 uM) |
| CL6 | 0% |
| SK0222 | 60% |
| (0422?) | 80% |
| SK0338F2 | 70% |
| SK0357F2 | 30% |
| SK0361 | 90% |
| SK0379 | 100% |
| SK0392 | 20% (50 uM) |
| SK0402 | 20% |
| SK0403 | 35% |
| SK0408 | 50% |
| SK0422 | 35% |
| SK0423 | 50% |
| SK0448 | 50% |
| SK0448F1 | 20% |
| SK0450 | 50% |
| SK0501 | 0% |
| SK0502 | 0% |
| SK0503 | 0% |
| SK0504 | 0% |
| SK0514 | 100% |
| SK0515 | 60% |
| SK0516 | 10% |
| SK0517 | 60% |
| SK0677 | 40% |
| SK0678 | 80% |
| SK0679 | 80% |
| SK0680 | 60% |
| SK0901 | 90% |
| SK0910 | 90% |
| SK0951 | 0% |
| SK0953 | 0% |
| SK0954 | 0% |
| VI072209-01 | 70% |
| VI072309-02 | 0% |
| CL1D | 80% |
| CL2D | 80% |
| SK0456 | 60% |
| SK0457 | 90% |
| SK0459F1 | 50% |
| SK0472 | 50% |
| SK0473 | 5% |
| SK0476 | 80% |
| SK0489 | 70% |

In the results of Table 1, there are a number of compounds illustrating positive results that inhibit the pigment effectively in fish embryos. However, A11 and its analogs additionally showed no developmental toxicity, with A11 being the most potent one. Other A-11 analogs showed different degrees of cardiac toxicity.

Testing the Skin-Whitening Efficacy after Compound Withdrawal

It has been reported that melanin usually reappears after the withdrawal of skin whitening products. Earlier results showed that the melanin reappearance is almost a hundred percent for most of the tested human skin-whitening products except for A11, revealing a unique property of A11. In confirmation of this result and also to test this effect of additional human skin-whitening drugs to see if any had the same effect as A11, according to Protocol 3, the zebrafish embryos were incubated with the compounds A11, MEK-I and PTU from 24-48 hpf or 24-64 hpf when the melanin is inhibited followed by wash off of the compounds. The pigmentation was monitored closely for 48-72 hours. Similarly, this experiment was repeated at least three times to gain a reproducible result.

Figure 6:
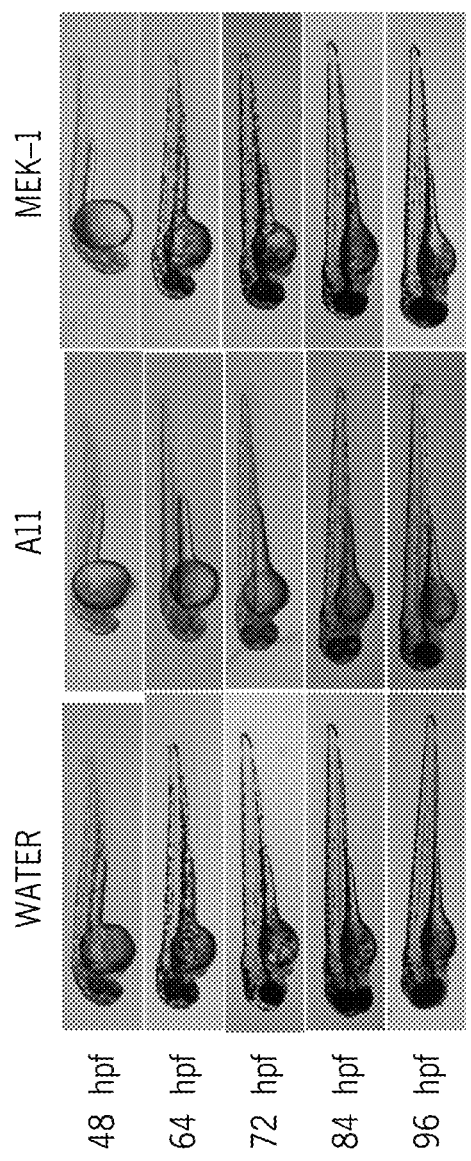
FIG. 6 are photo illustrations and a graph showing when treated 24-48 hpf or 64 hpf, MEK-I and PTU completely recover to 100% pigmentation by 72 hpf. Interestingly, A11 only recovers 50% of its pigment.
Figure 6:
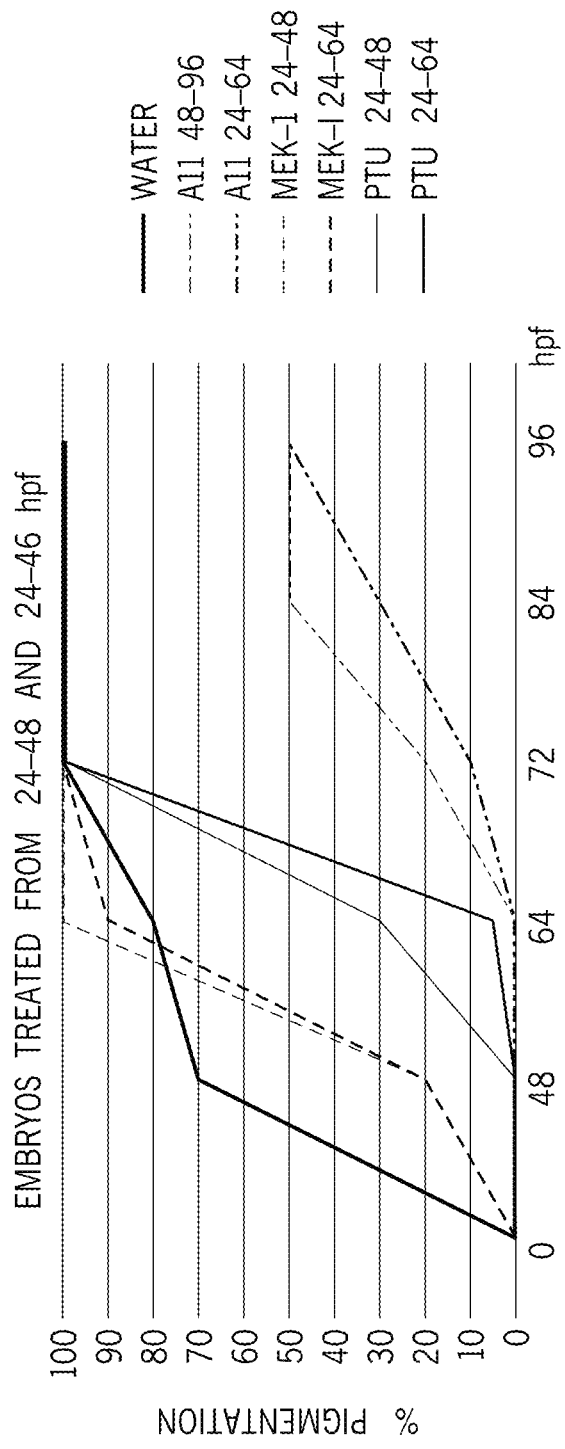

In reference to FIG. 6, the results show that:
all of the compounds tested over all time periods recover completely to 100% of pigmentation, with the exception of A-11, which only recovers to approximately 50% of pigmentation.

Molecular Mechanisms of A11 and MEK-I

Figure 22:
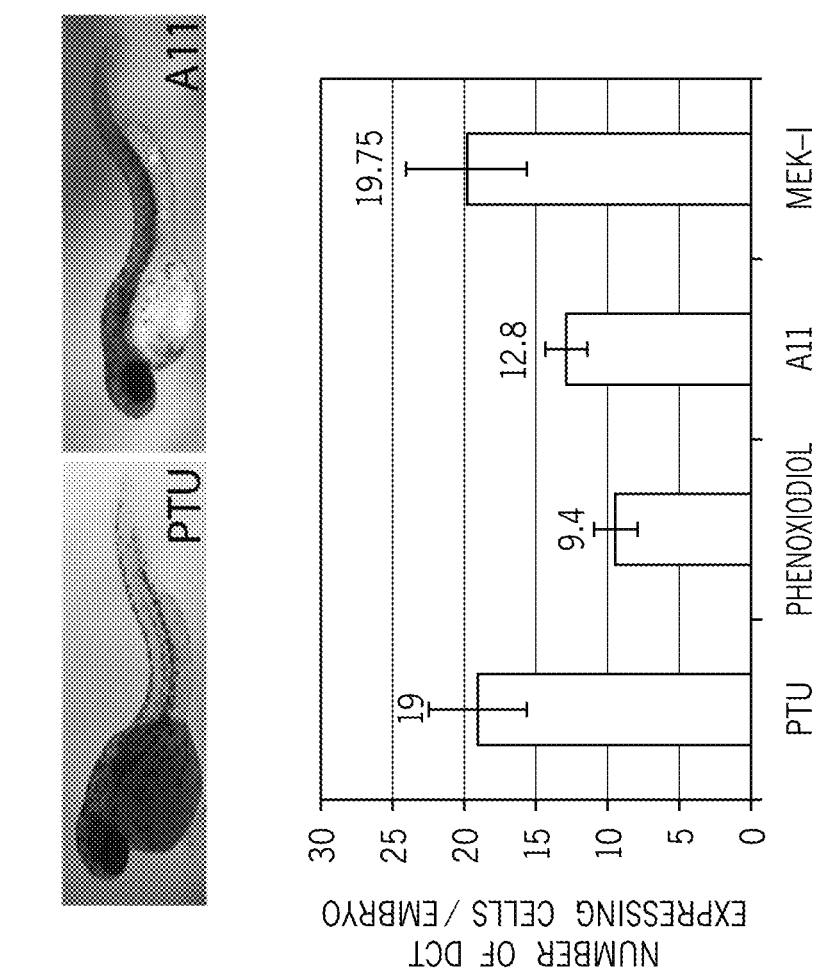
FIG. 22 is a graph of the number of dct-expressing cells in embryos with various compositions.

To further understand the mechanism of A11, we examined the development of melanocytes by in situ hybridization for the dct (dopachrome tautomerase) gene which is expressed in differentiated melanocytes. The results illustrated in FIG. 22 showed that the number of dct-expressing cells in A11-treated embryos is significantly lower than in the control.

Figure 21:
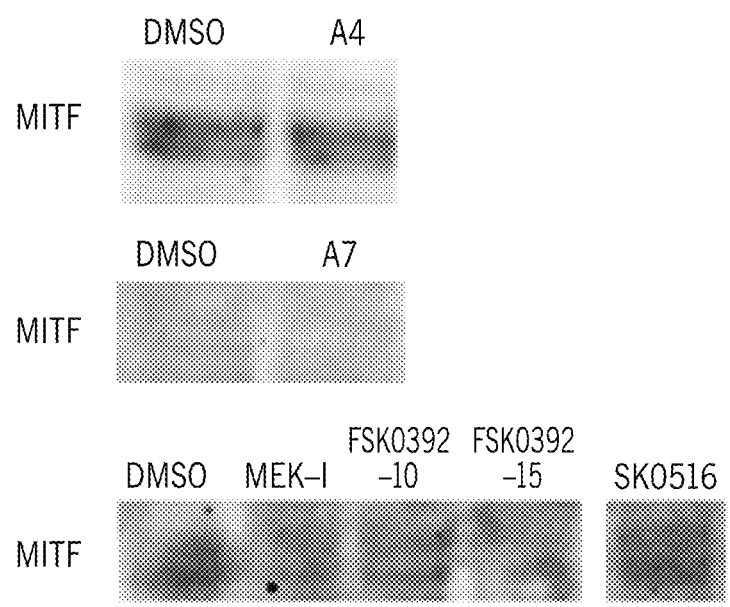
FIG. 21 is a representation of Western blot analyses for the MITF protein levels as a result of application of A11 analogs.
Figure 23A:
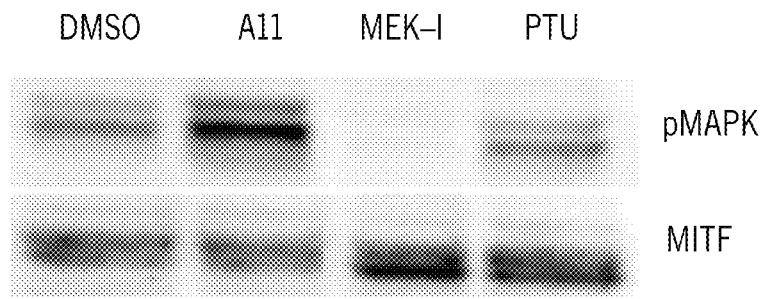
FIG. 23A are graphs of the effects of A11 and other compounds on MAPK and MITF activities.
Figure 23B:
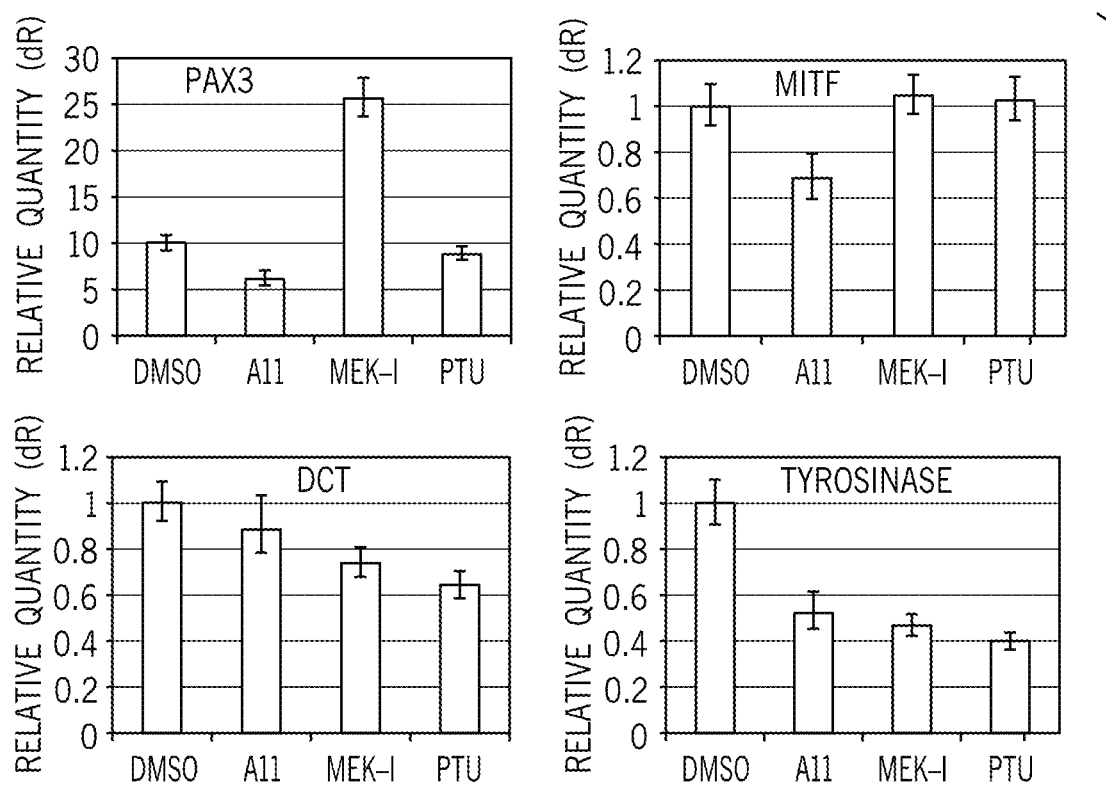
FIG. 23B are graphs of effects of compounds on PAX3, MITF, DCT and Tyrosinase expression.

To understand how A11 inhibits melanoma proliferation, we examined the MITF expression level in A11-treated B16-F10 cells by western blot and RT-qPCR. Interestingly, MITF protein is distinguishably lower than that in the DMSO control (FIG. 21). The decreased MITF protein is consistent with the lower amount of MITF mRNA indicated by the RT-qPCR result. We went on to examine the upstream genes of melanocyte differentiation Pax3 and found that A11 also reduces Pax3 expression. In addition, the DCT (dopachrome tautomerase) and tyrosinase expression was also decreased by A11 as well as MEK-I. These results suggest that A11 regulates melanocyte differentiation. Interestingly, MEK-I caused high level of MITF in the western blot but not in RT-qPCR, indicating inhibition of MAPK pathway may lead to stabilization of MITF protein but has no effect on the MITF transcription. Another interesting result is that MEK-I increases Pax3 transcription as shown in FIG. 23.

Chemotherapeutic Treatment

In addition to the efficacy of compounds A11 and other related compounds in the inhibition of pigment/melanin formation, further testing of the compounds has disclosed a finding that the A11 and the analog SK-03-92 inhibit the formation of melanoma cells, thereby providing potential chemotherapeutic compounds.

Looking at FIGS. 7-13, using normal zebrafish embryos, a transgenic zebrafish line that produces melanoma, and a mouse melanoma cell line, the A11 and SK-03-92 compounds inhibited the formation and recovery of melanoma in transgenic zebrafish embryos (inhibit melanoma cancerous cell proliferation), in addition to the inhibition of pigment/melanin formation. Using the mouse cell line B16-F10, it was found that A11 and SK-03-92 caused a decrease of melanin as well as the cell number. In comparison with other well-known skin-lightening compounds, it was found that A11 and SK-03-92 caused almost no detectable toxicity in the developing embryos. In addition, preliminary studies on the molecular mechanism for these compounds appears to suggest that A11 and SK-03-92 have a different and novel molecular mechanism from FDA-approved melanoma drugs, such as cobimetinib and decarbazine. With these results, A11, SK-03-92 and other analogs may prove to be effective drugs for the treatment of melanoma cancer.

Figure 7:
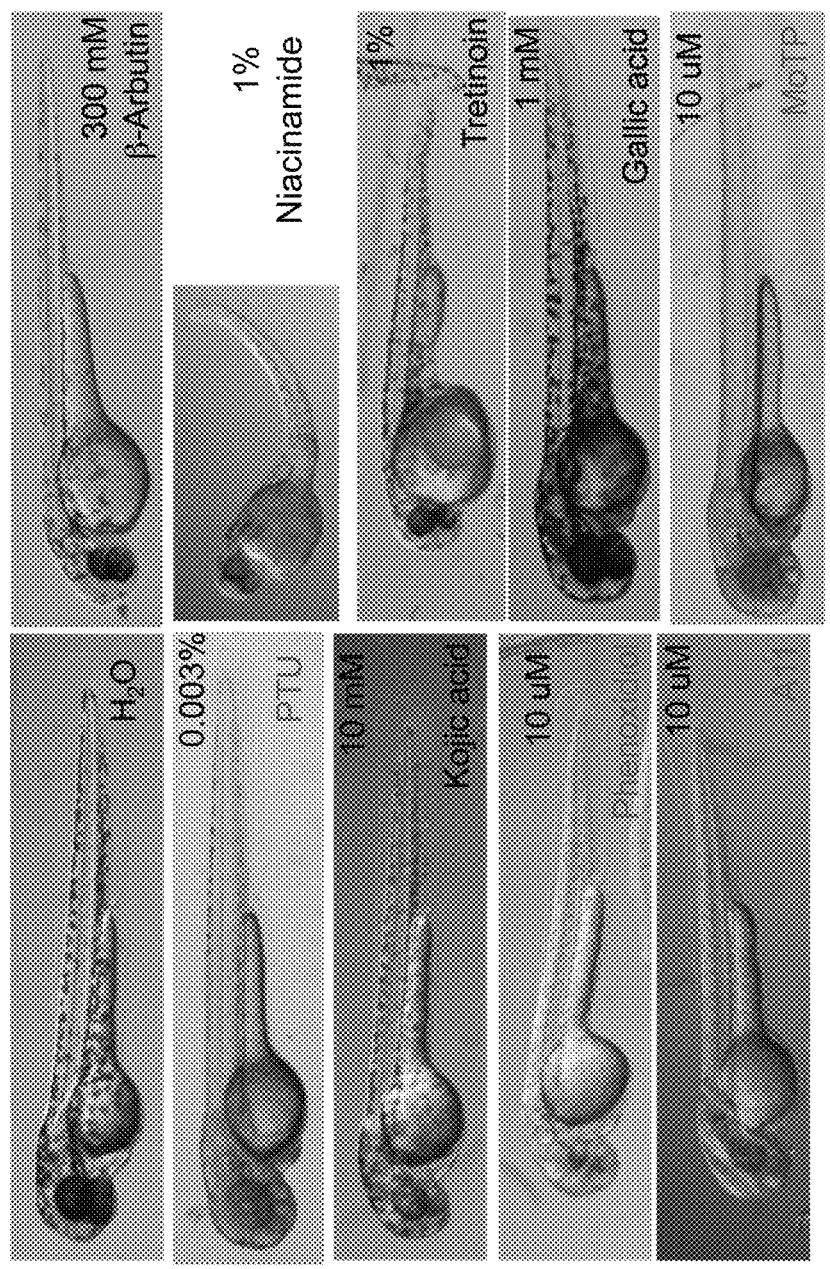
FIG. 7 are photo illustrations of the pigmentation inhibition in all normal zebrafish embryos with exemplary embodiments of the human drug treatments of the present invention.
Figure 8:
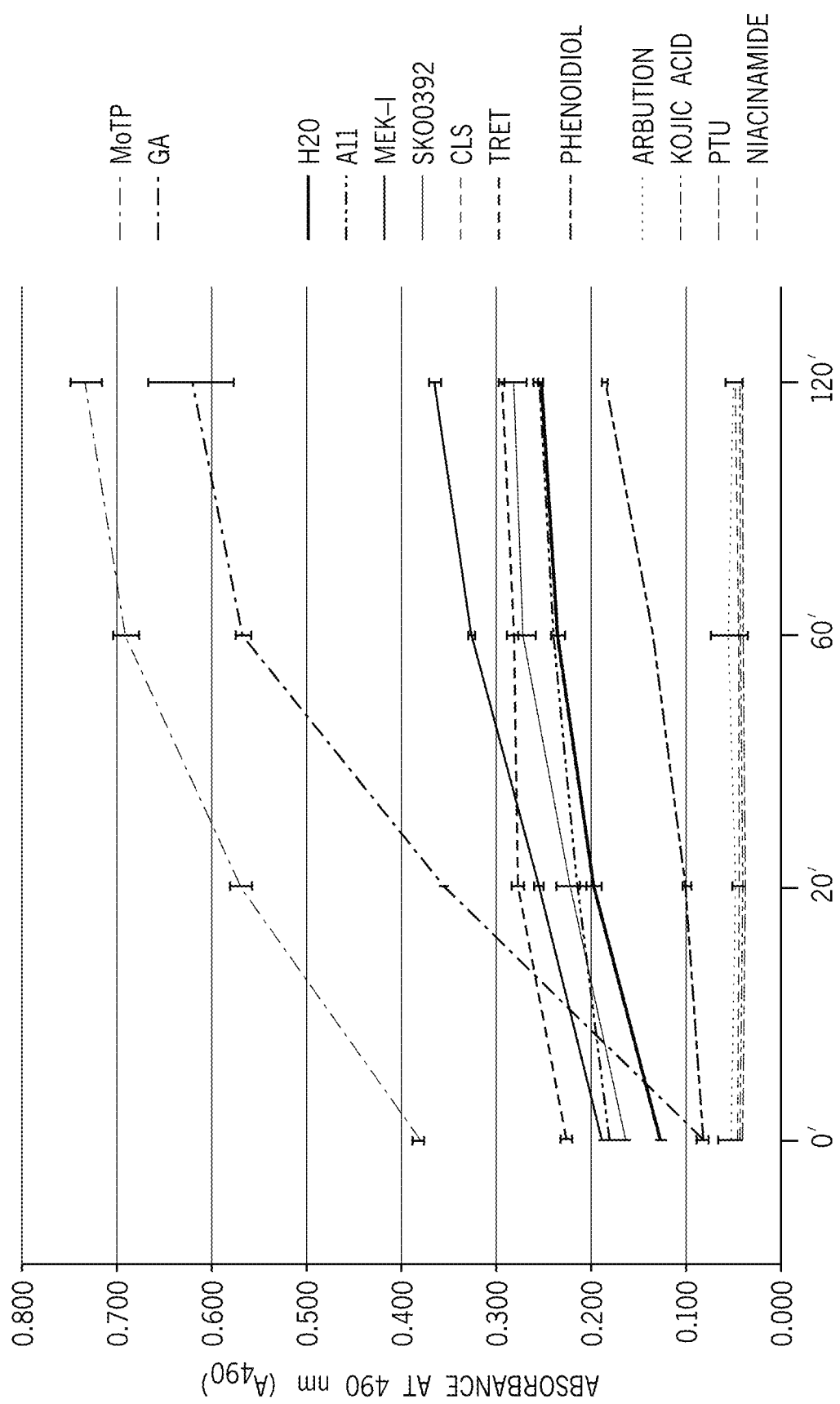
FIG. 8 is a graph of the effects of various pigment reducing compositions on tyrosinase expression.
Figure 9:
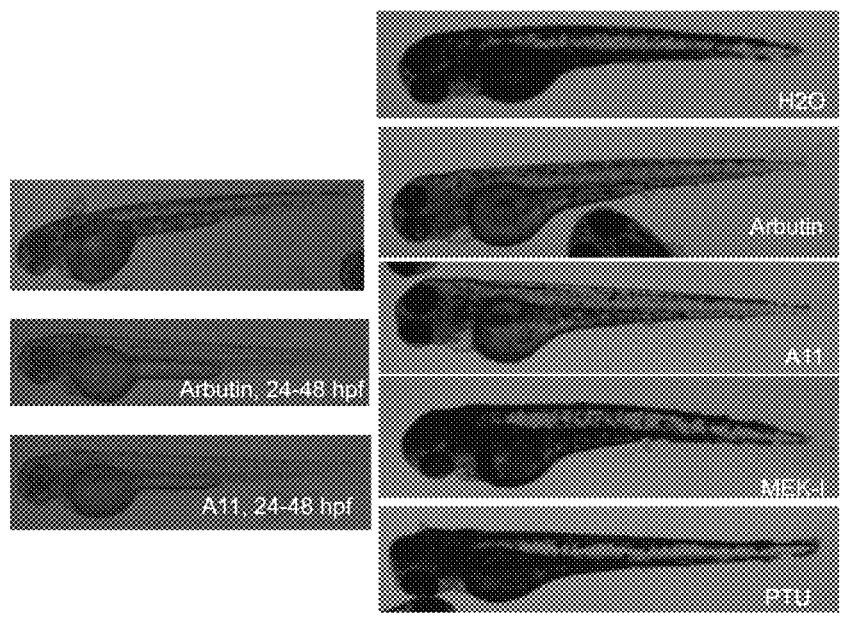
FIG. 9 are photo illustrations of the melanoma inhibition in transgenic melanoma zebrafish embryos with exemplary embodiments of the human drug treatments of the present invention.
Figure 10:
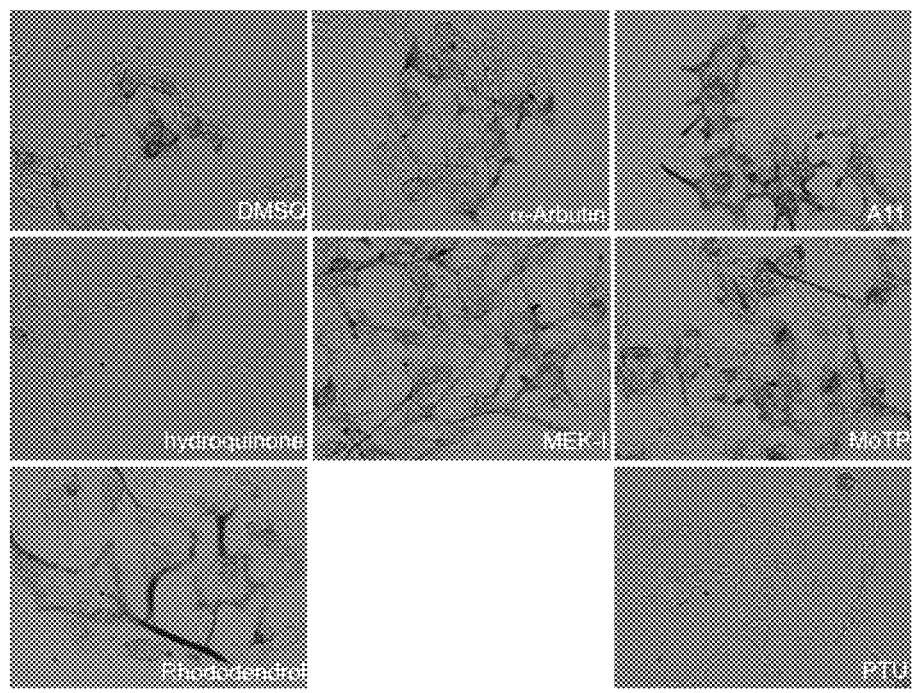
FIG. 10 is are photo illustrations of melanin cells treated with various pigment whitening compositions.
Figure 11:
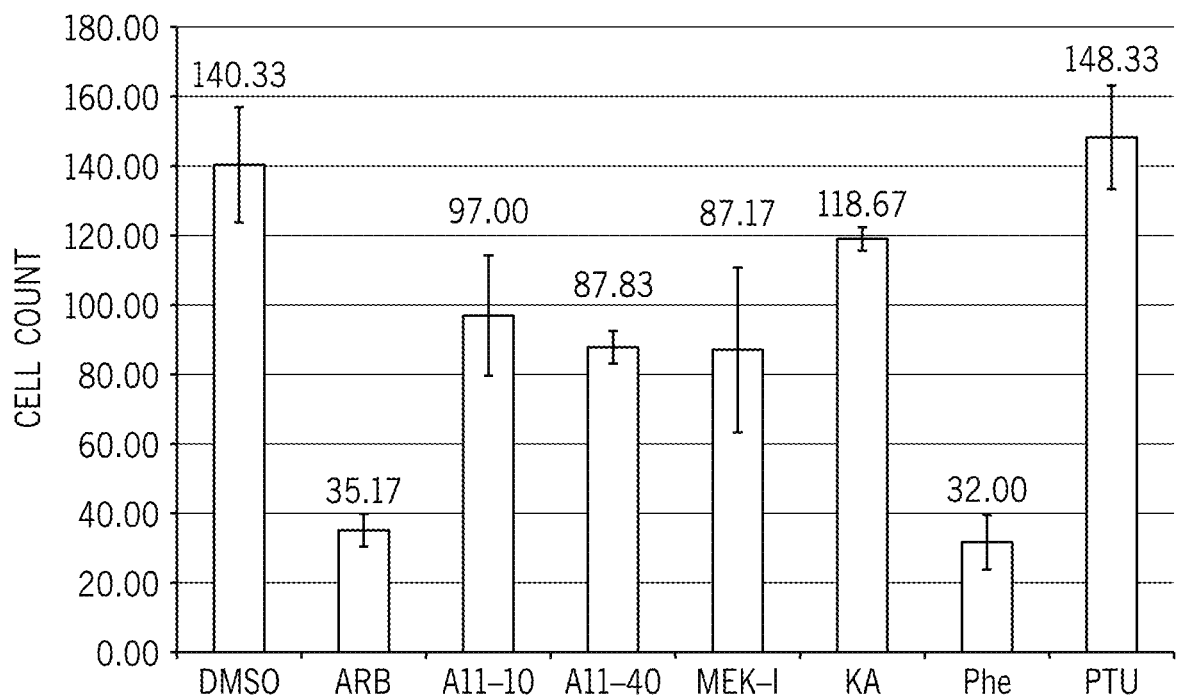
FIG. 11 is a graph of the effects of various pigment reducing compositions including A11 on melanoma cell proliferation.
Figure 12:
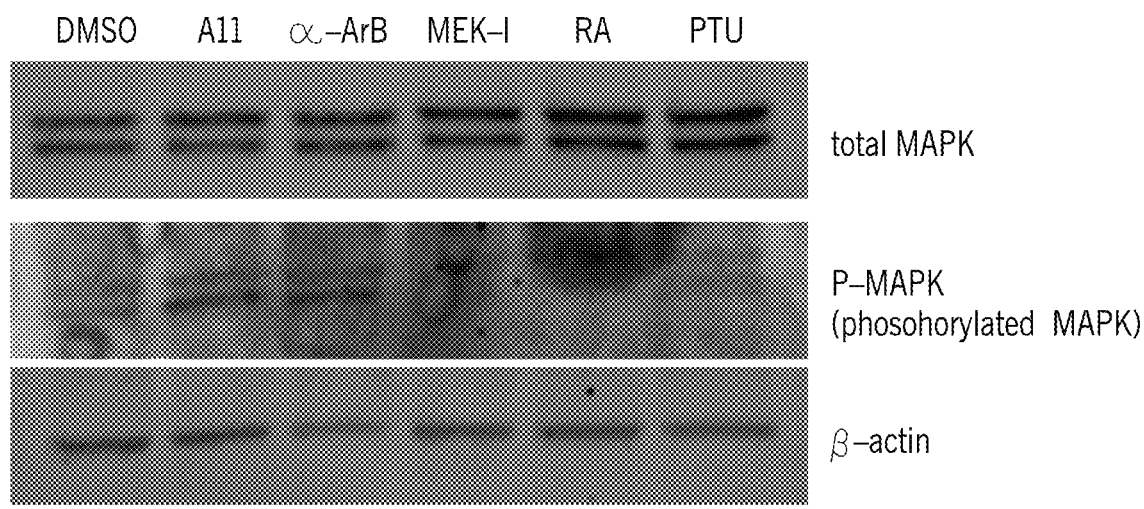
FIG. 12 are photo illustrations of MEK activity with exemplary embodiments of the human drug treatments of the present invention.

In particular, in FIG. 7 it is illustrated that A11 inhibits pigmentation formation, but in FIG. 8 A11 is shown not to inhibit tyrosinase formation. Further, in FIGS. 9-12 A11 is shown to inhibit both the formation of melanoma and the recovery of melanoma in transgenic melanoma zebrafish embryos while increasing MEK activity. The intracellular signaling pathway that involves Raf and MEK is known to be the major pathway to regulate cell proliferation. Many current melanoma drugs such as cobimetinib works by inhibiting Raf or MEK. While they are effective in inhibiting melanoma growth, they exert different degrees of side effect on normal cells by inhibiting the Raf-MEK pathway. The fact that our compounds A11 and SK0392 are able to inhibit melanoma growth while increasing MEK activity suggests that they might be a novel melanoma drug with reduced side effects. Also, with regard to FIG. 13, the compound SK-03-92 is shown to inhibit melanoma cell growth by approximately 10% at 10 μM and at 100% at 40 μM.

In further experimentation, the efficacy and characterization of the molecular mechanism of A11 were investigated.
1) The EC50 of A11 was determined to be around 40 μM which is close to the inhibitor of MEK which is a molecular target in the therapies for many cancers.
2) We identified several A11 analogs that can also inhibit melanoma growth, albeit with lower efficacy.
3) A11 does not seem to cause high toxicity to normal melanocytes.
4) Cell biology studies revealed that A11 reduces mitosis but does not induce apoptosis in melanoctyes.
4) It is confirmed that A11 and several analogs significantly increase the MAPK activity, strongly suggesting a novel mechanism in inhibiting melanoma growth.
5) Preliminary results from qPCR and western blot suggest that A11 suppresses melanocyte differentiation.

To find out the effective concentration (EC) and lethal concentration (LC) of A11, both melanoma and normal melanocyte cells will be treated with A11 and FSK-03-92 at different concentrations. We will define the $EC_{50}$ and $LC_{50}$ for the compounds.

Results:

A. EC50 of A11 on Melanoma Inhibition.

Figure 14:
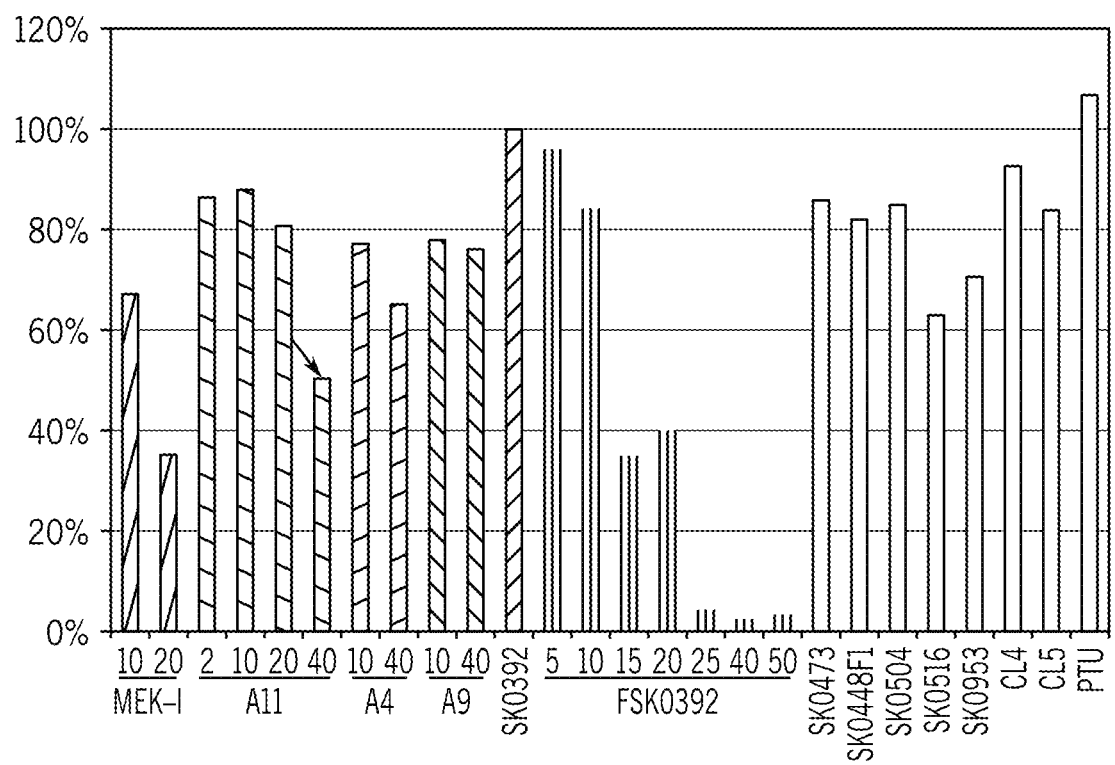
FIG. 14 is a graph of growth inhibition on melanoma cells by A11 analogs.

The graph in FIG. 14 shows that A11 at 40 μM causes 50% cell proliferation (arrow) compared to the control. Thus the EC50 of A11 in inhibiting melanoma growth is about 40 μM, but no cell death was observed in any of the tested concentrations of A11. However, in earlier experiments, we identified SK-03-92 as a potent A11 analog. We found that FSK-03-92, a fluorinated derivative of SK-03-92, actually killed melanoma cells as many cells were found to be dead and floating in the medium. At 25 μM or higher, FSK-03-92 caused near 100% death and the LC50 of FSK-03-92 was about 12 μM. In addition, several other A11 analogs show potential inhibition, such as A4 and SK-05-16.

B. EC50 of A11 on Normal Melanocyte

Figure 15:
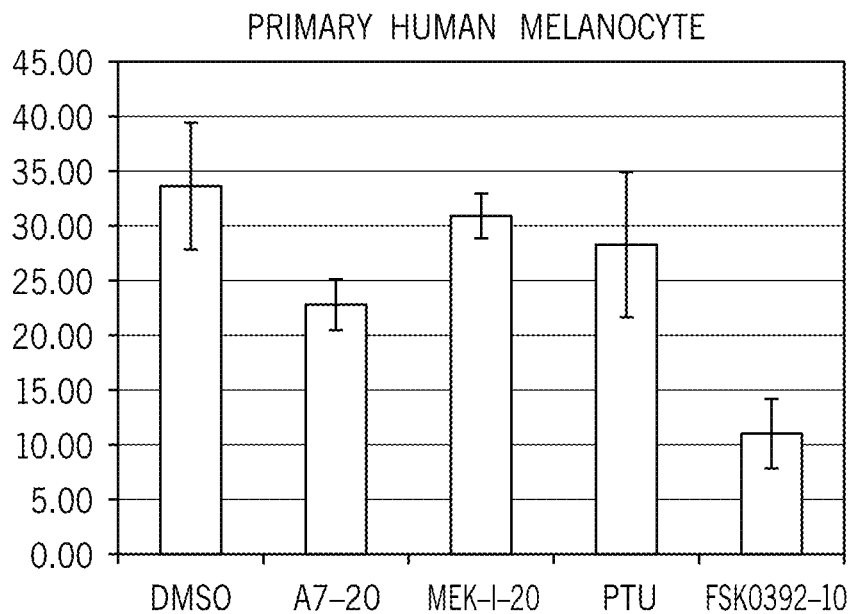
FIG. 15 is a graph of growth inhibition on normal human melanocytes by A11 analogs.

We used primary human melanocytes for this experiment, the results of which are shown in FIG. 15. These cells proliferate slowly making it difficult to gather enough cells for experiments with all the A11 analogs. In the first experiment, A11 was tested at 10 μM and did not show any inhibition. In the second experiment, A7 and a few other compounds were evaluated. The results show that A7 at 20 μM slightly inhibits the growth of normal melanocytes, suggesting A11 might also inhibit normal melanocyte proliferation. More interestingly, FSK-03-92, fluorinated SK03-92, was found to be very toxic to normal melanocytes. At 10 μM, FSK-03-92 caused near 80% lethality (comparing with the 20% kill by 10 μM FSK-03-92 on melanoma cells in FIG. 14).

1) Near 40 A11 derivatives were available for testing and all derivatives were tested to identify additional positive and possibly more potent drugs.

Figure 13:
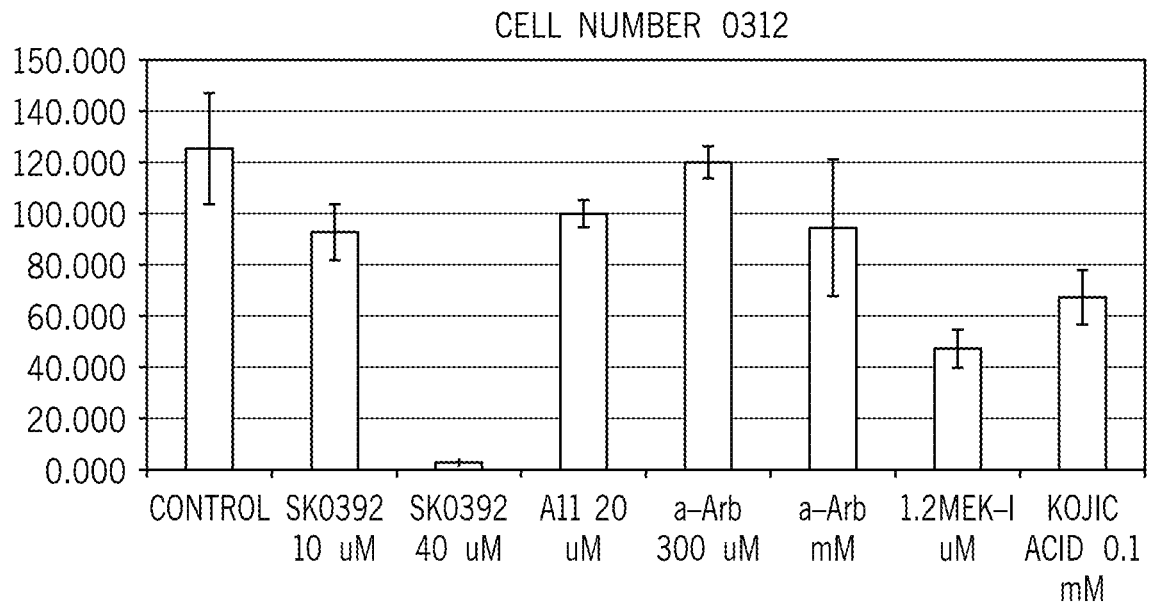
FIG. 13 is a graph of the effects of various pigment reducing compositions including A11 and SK-03-92 on melanoma cell proliferation.

All the A11 analogs were tested at 20 μM, and most of them did not show inhibition on melanoma cells except those shown in FIG. 13. Again, the results suggest several potential A11 substitutes: A4, SK-05-16, and SK-09-53.

These results regarding the inhibition of growth of melanin/melanoma are also shown in the following Table 2, which includes those compounds that showed pigment inhibition on fish embryos, and in Table 3, where the growth inhibition results are averaged to illustrate those compounds with potential for melanoma therapy (<65%) and toxicity (<10%). (MEK-I is a known MEK inhibitor as a comparison purchased from Sigma):

TABLE 2

Effects on Compounds On Melanoma Growth

| Cmpd-μM | Melanin | Growth |
|---|---|---|
| MEK-I-10 | 104%, 78%, 94% | 72%, 62% |
| MEK-I-20 | 82%, 84% | 47%, 20%, 38% |
| A11-2 | 99% | 86% |
| A11-10 | 104%, 84%, 97%, 95%, 100% | 88%, 92%, 101%, 69% |
| A11-20 | 101%, 92% | 81%, 80% |
| A11-40 | 84%, 68%, 56% | 60%, 63%, 28% |
| A3-20 | 89% | |
| A4-10 | 95% | 77% |
| A4-40 | 83% | 65% |
| A5-20 | 89% | |
| A7-20 | 89% | |
| A9-10 | 101% | 78% |
| A9-40 | 96% | 76% |
| SK0392-10 | 97% | 100% |
| FSK0392-5 | 95% | 96% |
| FSK0392-10 | 78%, 89%, 83% | 79%, 74%, 99% |
| FSK0392-15 | 79% | 35% |
| FSK0392-20 | 80%, 70% | 20%, 61% |
| FSK0392-25 | 69% | 4% |
| FSK0392-40 | 65%, 56% | 2%, 20% |
| FSK0392-50 | 64% | 3% |
| SK0473-20 | 95% | 86% |
| SK0448F1-20 | 98% | 82% |
| SK0504-20 | 95% | 85% |
| SK0516-20 | 80% | 63% |
| SK0953-20 | 96% | 71% |
| CL4-10 | 107% | 93% |
| CL5-10 | 96% | 84% |
| PTU | 59%, 67%, 89%, 67%, 64% | 87%, 107%, 128%, 106% |

TABLE 3

Effect of Compounds on Melanoma Growth

| Cmpd-μM | Average Melanoma growth (from the previous chart) |
|---|---|
| MEK-I-10 | 67% |
| MEK-I-20 | 35% |
| A11-2 | 86% |
| A11-10 | 88% |
| A11-20 | 81% |
| A11-40 | 50% |
| A3-20 | |
| A4-10 | 77% |
| A4-40 | 65% |
| A5-20 | |
| A7-20 | |
| A9-10 | 78% |
| A9-40 | 76% |
| SK0392-10 | 100% |
| FSK0392-5 | 96% |
| FSK0392-10 | 84% |
| FSK0392-15 | 35% |
| FSK0392-20 | 40% |
| FSK0392-25 | 4% |

TABLE 3-continued

Effect of Compounds on Melanoma Growth

| Cmpd-µM | Average Melanoma growth (from the previous chart) |
|---|---|
| FSK0392-40 | 2% |
| FSK0392-50 | 3% |
| SK0473-20 | 86% |
| SK0448F1-20 | 82% |
| SK0504-20 | 85% |
| SK0516-20 | 63% |
| SK0953-20 | 71% |
| CL4-10 | 93% |
| CL5-10 | 84% |
| PTU | 107% |

Figure 16:
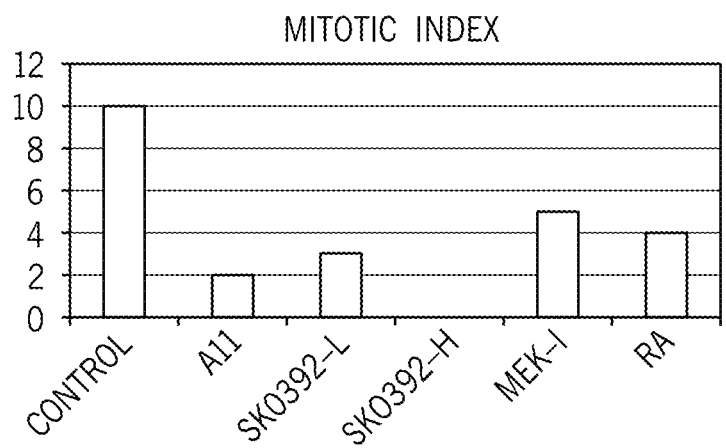
FIG. 16 is a graph of the mitotic index of melanoma cells.
Figure 17:
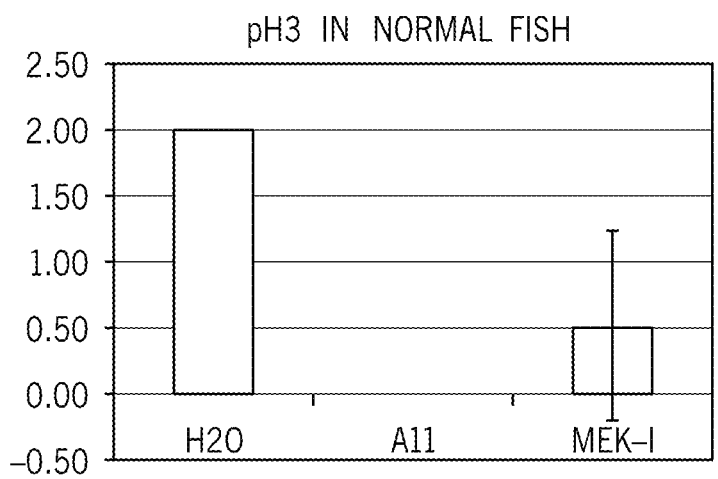
FIG. 17 is a graph of the mitotic index of melanocytes in zebrafish embryos.

Results:

A. To confirm the growth inhibition on melanoma cells by A11, as shown in FIG. 16, the mitotic index, i.e. the number of cells undergoing mitosis, was determined using the anti-phospho-histone H3 antibody. A11-treated melanoma cells had significantly lower mitotic index. The same conclusion was obtained when using zebrafish embryo, as illustrated in FIG. 17. These results support the conclusion that A11 inhibits the proliferation of melanoma and normal melanocytes.

Figure 18A:
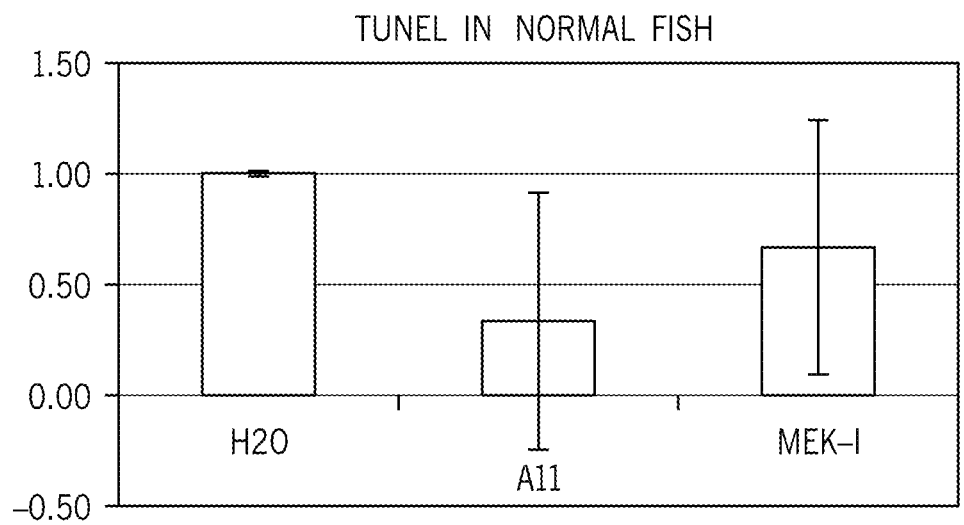
FIGS. 18A and 18B are graphs of melanocyte apoptosis by A11 in normal (FIG. 18A) or melanoma forming (FIG. 18B) zebrafish embryos.
Figure 18B:
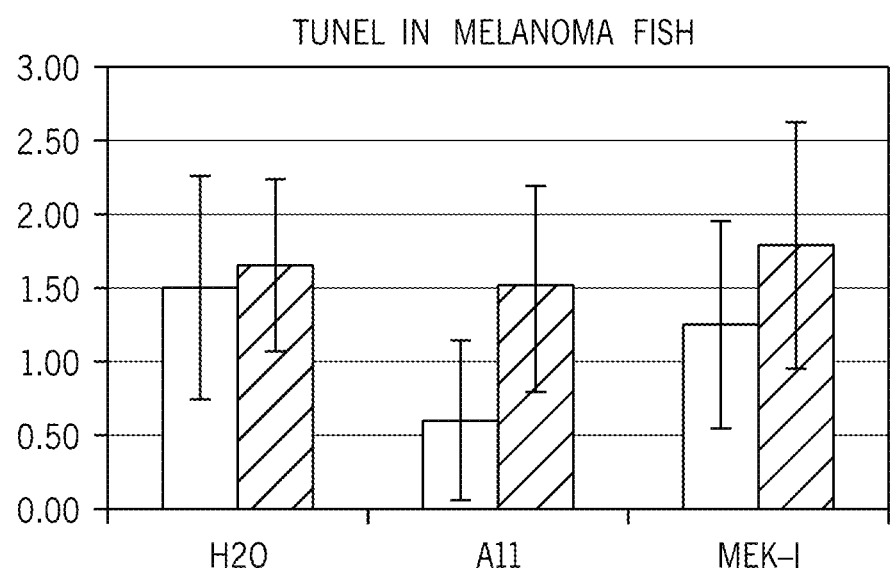

B. Observations from the cell proliferation experiments (FIG. 14) suggest that A11 does not cause cell death. To confirm this, TUNEL experiments were performed on melanoma cells, with the results shown in FIGS. 18A-18B in which the TUNEL assay on both normal and transgenic melanoma-forming zebrafish embryos, the results showed no significant difference, suggesting A11 does not cause cell death in melanocytes.

2) One of our earlier experiments revealed the association of elevated MAPK activity, a gene associated with cell proliferation, and decreased melanoma cell growth. We wanted to further understand the molecular mechanism of A11 and its derivatives by examining the activities of MAPK, Akt, and PRPP pathways which regulate cell proliferation and cell death.

Figure 19A:
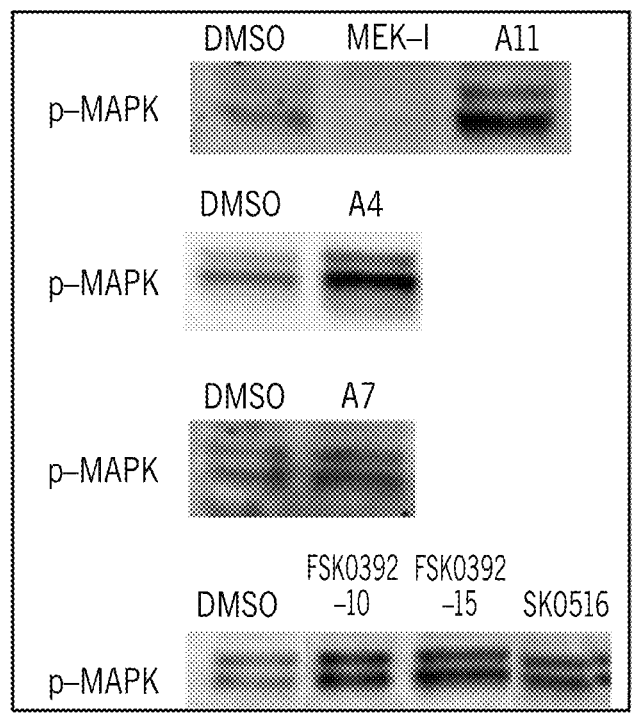
FIGS. 19A and 19B are graphs of the effects of A11 and its analogs on MAPK (FIG. 19A) and AKT activities (FIG. 19B).
Figure 19B:
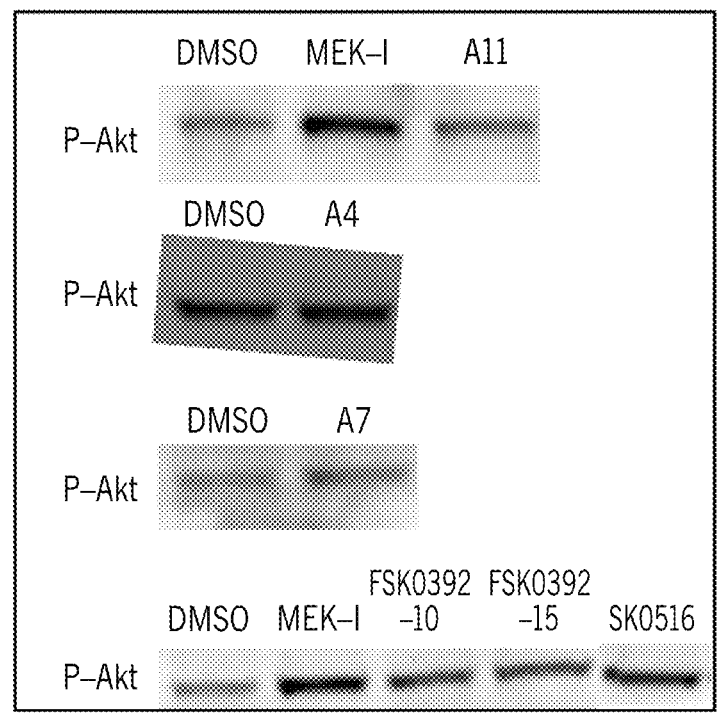

Results:

MAPK is involved in the major cell proliferation signaling pathway. In many cancer cells, MAPK is activated at high level by phosphorylation. Using the anti-phosphorylated-MAPK (p-MAPK) on western blot, it is very easy to understand the proliferation ability in cells. In FIG. 19A, the western blot using melanoma cells show that, while MEK-I effectively suppresses the amount of p-MAPK which correlated with the growth inhibition as expected, A11 and several analogs, including A4, A7, FSK-03-92 (at 10 and 15 µM), and SK-05-16, surprisingly increases the amount of p-MAPK. While the results are against our hypothesis and current understanding, it raises a very interesting mechanism of A11 which requires further investigation. Similarly, the Akt activity of these compounds was examined with the result shown in FIG. 19B. The results show slight increase of phosphorylated Akt by A11 and several analogs. The current understanding is that activated MAPK and Akt both lead to cell proliferation. Our results clearly do not fit into the current model and suggest a novel mechanism to inhibit cancer cell growth by A11.

3) In our earlier quantitative PCR experiments, the mit-f gene was expressed at high level in A11-treated melanoma cells. High mit-f expression has been shown to cause melanocyte differentiation and decrease or even cease of cell proliferation. To investigate whether A11 inhibits melanoma growth by enhancing melanoma cell differentiation which, if proved, will be a novel mechanism than all the current melanoma drugs, mit-f expression is examined at transcriptional and translational levels and the expression of other melanocyte differentiation genes.

Figure 20:
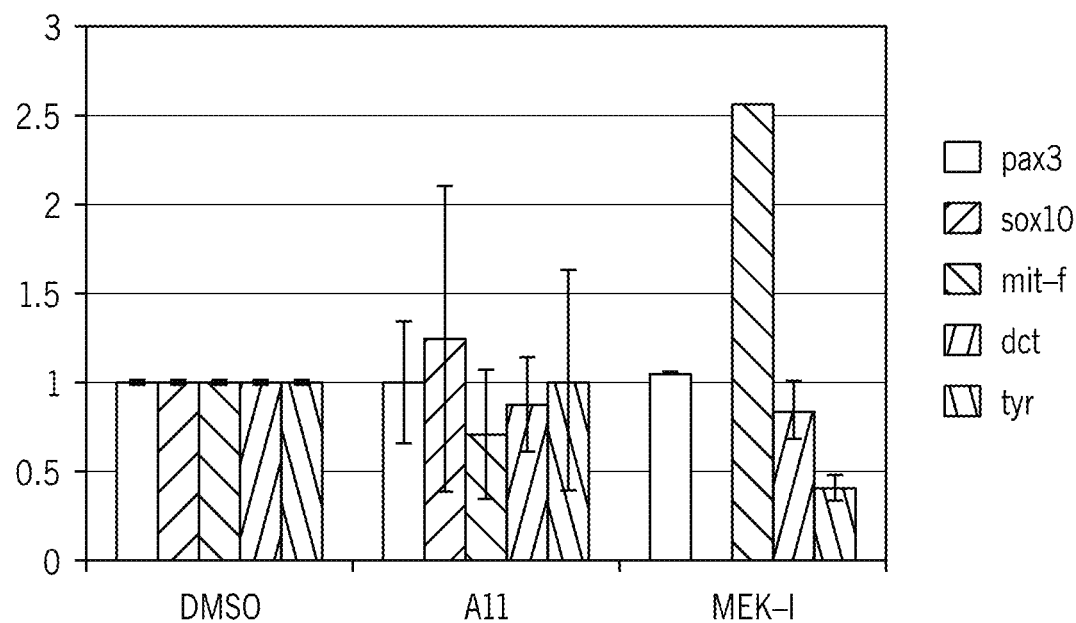
FIG. 20 is a graph of qPCR analyses for melanocyte differentiation genes as a result of application of A11 analogs.

Results:

The results of several qPCR experiments using melanoma cells were compiled in FIG. 20. Pax3 and sox10 are genes determine the melanocyte precursors while mit-f is the specific transcription factor that initiates melanocyte differentiation. Dct and tyr genes are expressed in differentiated melanocytes. It seems like A11 decreases the expression of mit-f gene. The decrease in magnitude is not significant likely due to the very heterogeneous cell types in melanoma.

Finally, the preliminary results of western blot analyzing MITF protein level (FIG. 21) show that A4 and A7 analogs cause slightly decrease of MITF protein, which is consistent with the qPCR results.

The following are the structures for some exemplary embodiments of the cancerous cell growth inhibiting compounds of the invention:

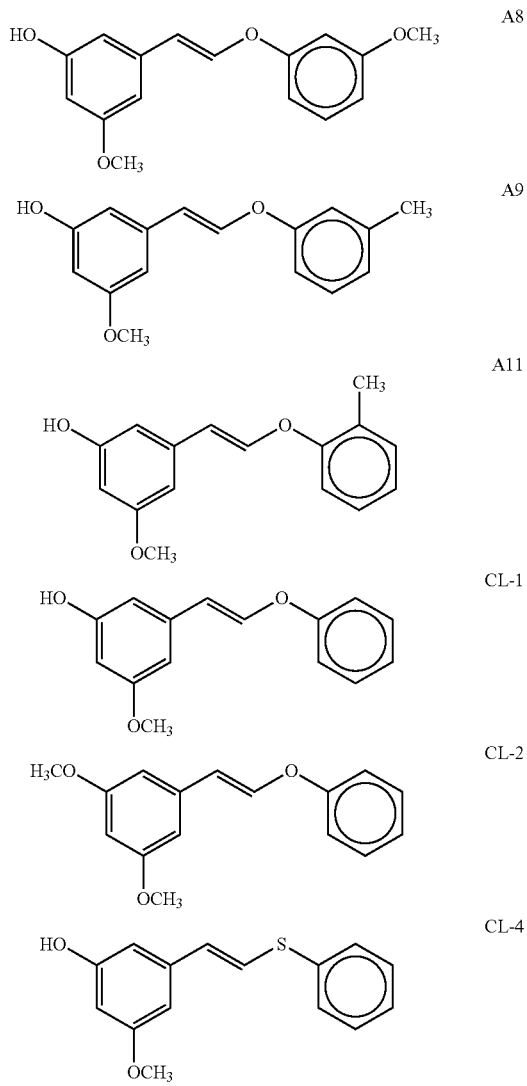

-continued

CL-6
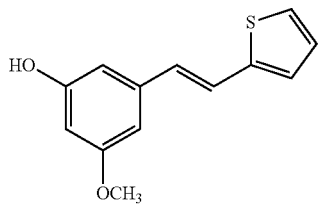

SK-03-92
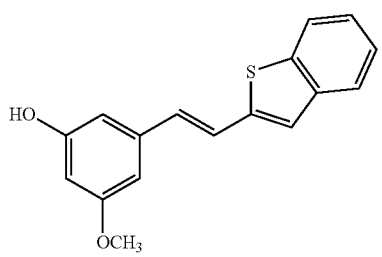

SK-09-51
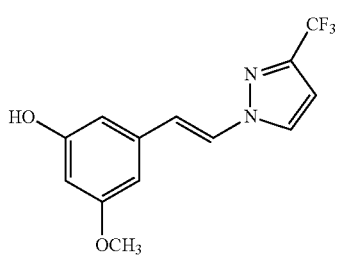

SK-09-53
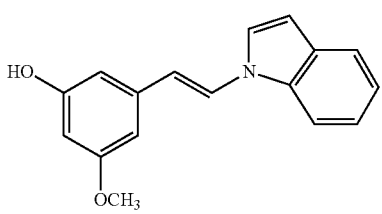

SK-09-54
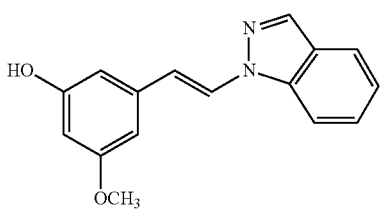

SK-04-73
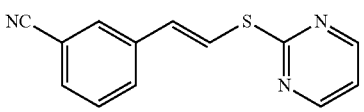

SK-05-01
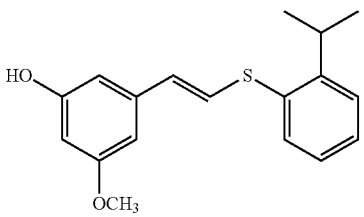

-continued

SK-05-02
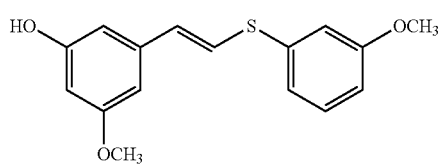

SK-05-03
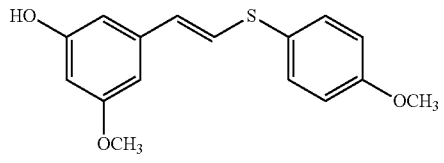

SK-05-04
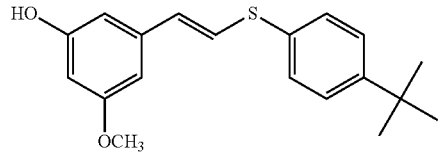

Other exemplary compound structures are found in co-owned U.S. Pat. No. 8,530,512, the entirety of which is expressly incorporated herein by reference for all purposes.

Chemical Synthesis

While testing on zebrafish embryos requires minimal amounts of compound, more A11 is needed for the subsequent assays with small mammals, e.g., guinea pigs. An efficient approach for the production of compound A11 and a number of its chemical analogs has been developed which is scalable and should allow for the preparation of the gram quantities of this agent required in this and subsequent investigations. Specifically, as shown in scheme 1 below, a copper-catalyzed coupling reaction will be used as the key step in the scale-up preparations of A11. Thus, after the key intermediate vinyl iodide 5 is synthesized (in four steps from commercially available dimethoxybenzyl alcohol 1), it may be coupled with commercially available 2-methylphenol to yield vinyl ether 6. Deprotection of 6 should then proceed cleanly to provide A11 in reasonable yields. Subsequent purifications will allow us to safely use this compounds as a potential skin whitening agent.

Scheme 1. Scheme for the Preparation of A11: 2-Methylphenyl-E-(3-hydroxy-5-methoxy)-styryl

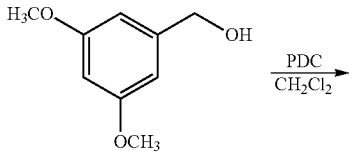

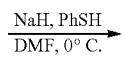

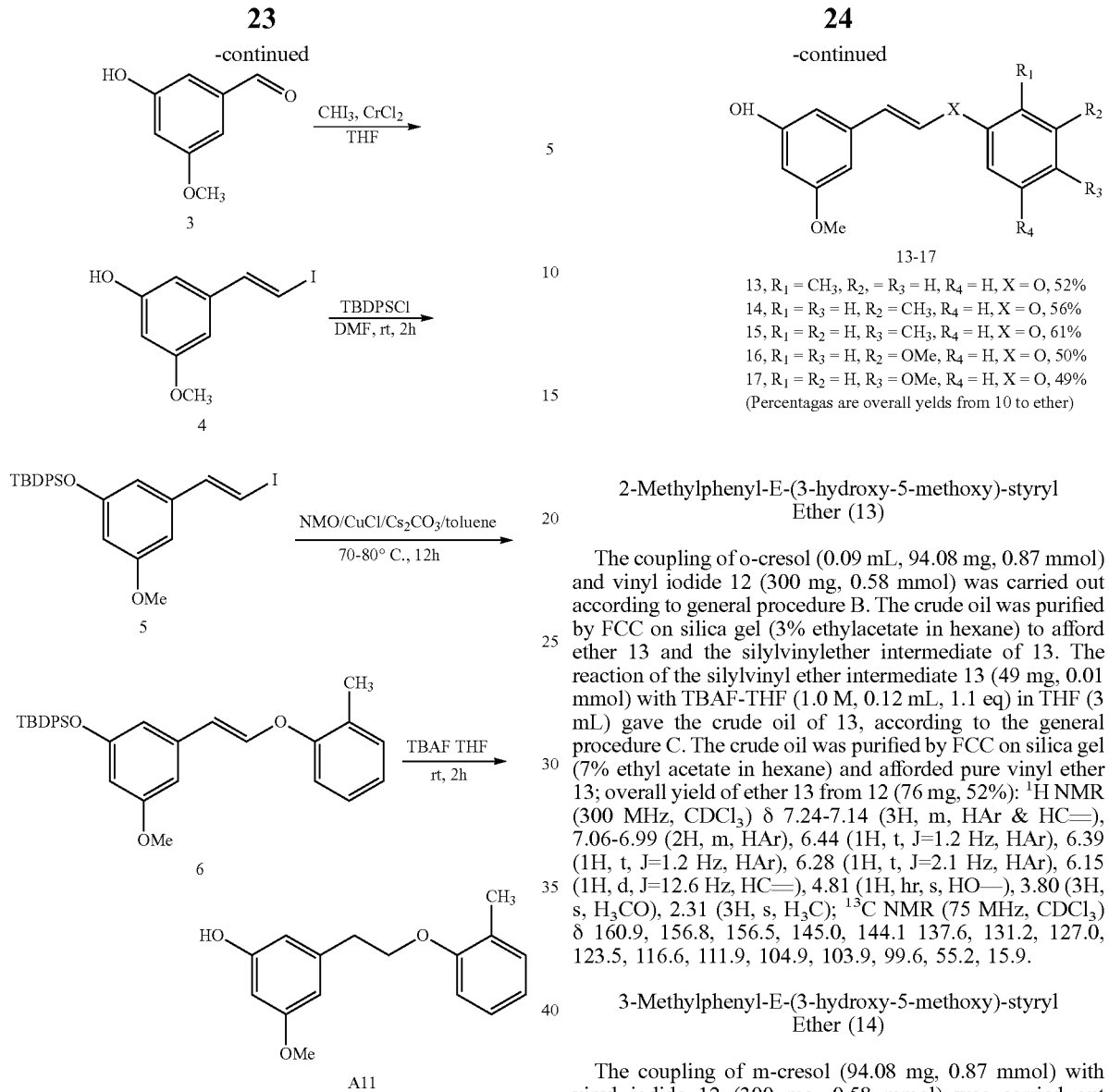

13-17
13, $R_1 = CH_3$, $R_2 = R_3 = H$, $R_4 = H$, $X = O$, 52%
14, $R_1 = R_3 = H$, $R_2 = CH_3$, $R_4 = H$, $X = O$, 56%
15, $R_1 = R_2 = H$, $R_3 = CH_3$, $R_4 = H$, $X = O$, 61%
16, $R_1 = R_3 = H$, $R_2 = OMe$, $R_4 = H$, $X = O$, 50%
17, $R_1 = R_2 = H$, $R_3 = OMe$, $R_4 = H$, $X = O$, 49%
(Percentages are overall yields from 10 to ether)

2-Methylphenyl-E-(3-hydroxy-5-methoxy)-styryl Ether (13)

The coupling of o-cresol (0.09 mL, 94.08 mg, 0.87 mmol) and vinyl iodide 12 (300 mg, 0.58 mmol) was carried out according to general procedure B. The crude oil was purified by FCC on silica gel (3% ethylacetate in hexane) to afford ether 13 and the silylvinylether intermediate of 13. The reaction of the silylvinyl ether intermediate 13 (49 mg, 0.01 mmol) with TBAF-THF (1.0 M, 0.12 mL, 1.1 eq) in THF (3 mL) gave the crude oil of 13, according to the general procedure C. The crude oil was purified by FCC on silica gel (7% ethyl acetate in hexane) and afforded pure vinyl ether 13; overall yield of ether 13 from 12 (76 mg, 52%): $^1$H NMR (300 MHz, CDCl$_3$) δ 7.24-7.14 (3H, m, HAr & HC=), 7.06-6.99 (2H, m, HAr), 6.44 (1H, t, J=1.2 Hz, HAr), 6.39 (1H, t, J=1.2 Hz, HAr), 6.28 (1H, t, J=2.1 Hz, HAr), 6.15 (1H, d, J=12.6 Hz, HC=), 4.81 (1H, hr, s, HO—), 3.80 (3H, s, H$_3$CO), 2.31 (3H, s, H$_3$C); $^{13}$C NMR (75 MHz, CDCl$_3$) δ 160.9, 156.8, 156.5, 145.0, 144.1 137.6, 131.2, 127.0, 123.5, 116.6, 111.9, 104.9, 103.9, 99.6, 55.2, 15.9.

3-Methylphenyl-E-(3-hydroxy-5-methoxy)-styryl Ether (14)

The coupling of m-cresol (94.08 mg, 0.87 mmol) with vinyl iodide 12 (300 mg, 0.58 mmol) was carried out according to general procedure B. The crude oil was purified by FCC on silica gel (5% ethyl acetate in hexane) to afford vinyl ether 14 and the silylvinyl ether intermediate of 14. The reaction of the silylvinyl ether intermediate of 14 (51 mg, 0.01 mmol) with TBAF●THF (1.0 M, 0.12 mL, 1.1 eq) in THF (3 mL) gave the crude oil of vinyl ether 14, according to general procedure C. The crude oil was purified by FCC on silica gel (5% ethyl acetate in hexane) to afford pure vinyl ether 14; overall yield of vinyl ether 14 from 12 (84 mg, 56%): $^1$H NMR (300 MHz, CDCl$_3$) δ 7.28-7.14 (2H, m, HAr & HC=), 6.96-6.87 (3H, m, HAr), 6.47 (1H, t, J=1.2 Hz, HAr), 6.42 (1H, t, J=1.2 Hz, HAr), 6.30 (1H, t, J=2.1 Hz, HAr), 6.24 (1H, d, J=12.3 Hz, HC=), 4.93 (1H, hr, s, HO—), 3.81 (3H, s, H$_3$CO), 2.38 (3H, s, H$_3$C); $^{13}$C NMR (75 MHz, CDCl$_3$) δ 161.0, 156.8, 156.7, 144.2, 139.9, 137.5, 129.4, 124.1, 117.6, 113.9, 112.8, 105.0, 104.1, 99.7, 55.2, 21.3; LRMS (EI), m/z (relative intensity): 256 [M]$^+$, 241, 91, 77, 63.

4-Methylphenyl-E-(3-hydroxy-5-methoxy)-styryl Ether (15)

The coupling p-cresol (94.08 mg, 0.87 mmol) with vinyl iodide 12 (300 mg, 0.58 mmol) was carried out according to A more generalized scheme for the preparation of A11 and other analogs, is shown below in Scheme 2.

Scheme 2. General Scheme for the O-vinylation of phenol or Substituted phenols by Reaction with 1-(E)-(3-hydroxy-5methoxy)-styryliodide, 10

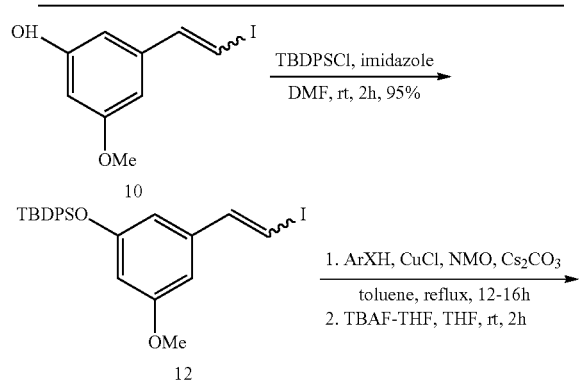

general procedure B. The crude oil was purified by FCC on silica gel (3% ethylacetate in hexane) to afford vinyl ether 15 and the silylvinyl ether intermediate of 15. The reaction of the silylvinyl ether intermediate of 15 (48 mg, 0.01 mmol) with TBAF●THF (1.0 M, 0.12 mL, 1.1 eq) in THF (3 mL) gave the crude oil of vinyl ether 15, according to the general procedure C. The crude ether was purified by FCC on silica gel (7% ethyl acetate in hexane) to afford vinyl ether 15; overall yield of vinyl ether 15 from 12 (75 mg, 51%): $^1$H NMR (300 MHz, CDCl$_3$) δ 7.18-7.12 (3H, m, HAr & 6.98-6.95 (2H, m, HAr), 6.45 (1H, t, J=1.2 Hz, HAr), 6.41 (1H, t, J=1.2 Hz, HAr), 6.29 (1H, t, J=2.1 Hz, HAr), 6.21 (1H, d, J=12.3 Hz, HC=), 5.21 (1H, hr, 5, HO—), 3.79 (3H, s, H$_3$CO), 2.35 (3H, s, H$_3$C); $^{13}$C NMR (75 MHz, CDCl$_3$) δ 161.0, 156.8, 144.6, 137.5, 135.4, 132.8, 130.1, 116.9, 112.5, 105.0, 104.0, 99.7, 55.2, 20.6; LRMS (EI), m/z (relative intensity): 256 [M]$^+$, 241, 91, 77, 65.

3-Methoxyphenyl-E-(3-hydroxy-5-methoxy)-styryl Ether (16)

The coupling of m-anisole (0.094 mL, 108.5 mg, 0.87 mmol) with vinyl iodide 12 (300 mg, 0.58 mmol) was carried out according to general procedure B. The crude oil was purified by FCC on silica gel (2% ethylacetate in hexane) to afford vinyl ether 16 and silylvinyl ether intermediate 16i. The reaction of the silylvinyl ether intermediate 16i (112 mg, 0.22 mmol) with TBAF●THF (1.0 M, 0.24 mL, 1.1 eq) in THF (3 mL) gave the crude oil of vinyl ether 16, according to the general procedure C. The crude oil was purified by FCC on silica gel (2% ethyl acetate in hexane) to afford vinyl ether 16; overall yield of vinyl ether 16 from 12 (79.5 mg, 50%). 16i: $^1$H NMR (300 MHz, CDCl$_3$) δ 7.78-7.74 (4H, m, HAr), 7.45-7.37 (6H, m, HAr), 7.28-6.26 (1H, HAr), 6.88 (1H, d, J=12.3 Hz, HC=), 6.69-6.57 (3H, n, HAr), 6.39 (1H, t, J=1.2 Hz, HAr), 6.35, (1H, t, J=1.2 Hz, 1-HAr), 6.22 (1H, t, J=2.1. Hz, HAr), 6.15 (1H, d, J=12.3 Hz, HC=), 3.83 (3H, s, H$_3$CO), 3.60 (3H, s, H$_3$CO); $^{13}$C NMR (75 MHz, CDCl$_3$) .δ 160.8, 160.5, 158.1, 156.8, 143.4, 134.9, 132.9, 129.8, 127.7, 113.4, 109.3, 108.9, 108.8, 104.9, 104.0, 103.0, 55.3, 55.0; LRMS (EI), m/z (relative intensity): 511 [M]$^+$, 454, 305 (100), 227, 77. 16: $^1$H NMR (300 MHz, CDCl$_3$) δ 7.29-7.26 (1H, m, HAr), 7.15 (1H, d, J=12.3 Hz, HC=), 6.70-6.62 (3H, m, HAr), 6.46 (1H, t, J=1.2 Hz, HAr), 6.41 (1H, t, J=1.2 Hz, HAr), 6.30 (1H, t, J=2.1 Hz, HAr), 6.25 (1H, d, J=12.3 Hz, HC=), 5.05 (1H, br, s, HO—), 3.83 (3H, s, H$_3$CO), 3.30 (3H, s, H$_3$CO); $^{13}$C NMR (75 MHz, CDCl$_3$) δ 161.0, 160.8, 158.1, 156.8, 143.8, 137.3, 130.1, 113.3, 109.0, 105.1, 104.1, 103.1, 99.9, 55.3, 55.2; LRMS (EI), m/z (relative intensity): 272 [M]$^+$, 255, 92, 77, 64.

4-Methoxyphenyl-E-(3-hydroxy-5methoxy)-styryl Ether (17)

The coupling of p-anisole (108.5 mg, 0.87 mmol) with vinyl iodide 12 (300 mg, 0.58 mmol) was carried out according to general procedure B. The crude oil was purified by FCC on silica gel (2% ethylacetate in hexane) to afford vinyl ether 17 and the silylvinyl ether intermediate of 17. The reaction of the silylvinyl intermediate of 17 (111 mg, 0.22 mmol) with TBAF●THF (1.0 M, 0.24 mL, 1.1 eq) in THF (3 mL) gave the crude oil of vinyl ether 17, according to the general procedure C. The crude oil was purified by FCC on silica gel (2% ethyl acetate in hexane) to afford pure vinyl ether 17; overall yield of vinyl ether 17 from 12 (77.8 mg, 49%): $^1$H NMR (300 MHz, CDCl$_3$) δ 7.10 (1H, d, J=12.3 Hz, HC=), 7.03-7.00 (2H, m, HAr), 6.91-6.88 (2H, m, HAr), 6.43 (1H, t, J=1.2 Hz, HAr), 6.39 (1H, t, J=1.2 Hz, HAr), 6.28 (1H, t, J=2.1 Hz, HAr), 6.15 (1H, d, J=12.3 Hz, HC=), 5.17 (1H, br, s, HO—), 3.82 (3H, s, H$_3$CO), 3.79 (3H, s, H$_3$CO); $^{13}$C NMR (75 MHz, CDCl$_3$) δ 161.0, 156.7, 155.7, 150.8, 145.4, 137.6, 118.4, 114.7, 111.9, 104.9, 103.9, 99.6, 55.6, 55.2; LRMS (EI), m/z (relative intensity): 272 [M]$^+$, 255, 134, 109, 77.

A scheme for the preparation of compound SK-03-92, is shown below in Scheme 3.

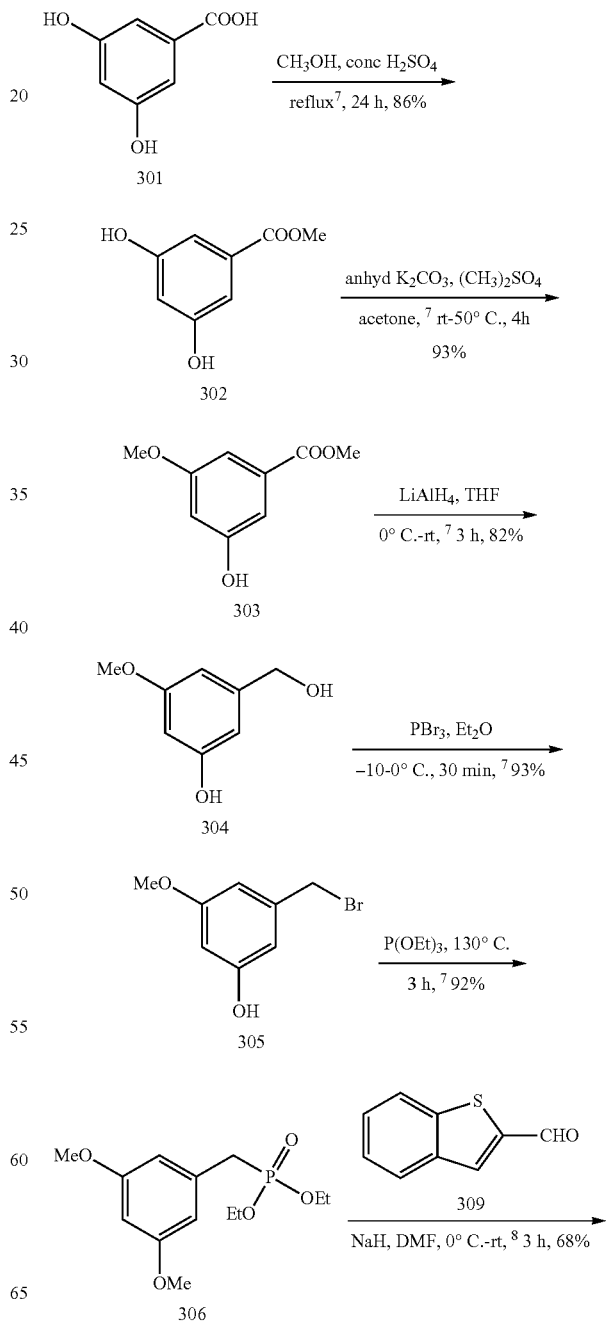

Scheme 3. Synthesis of 3-(E)-2-(benzo[b]thiophen-2-yl)vinyl-5methoxyphenol, SK-03-92

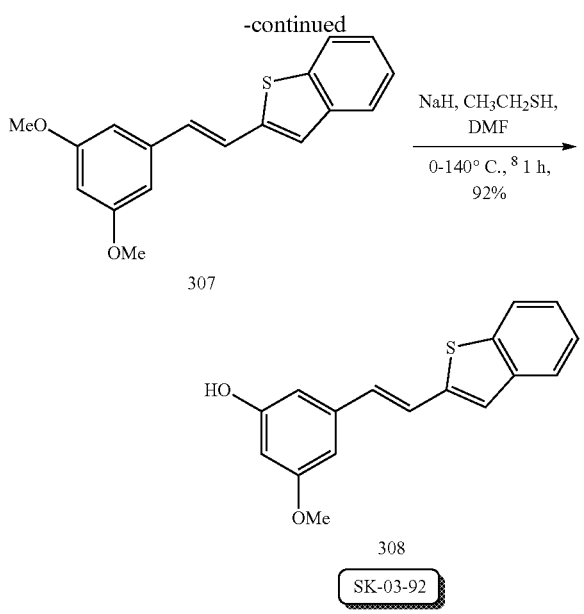

307

308

SK-03-92

3, 5-Dihydroxy Methylbenzoate (302)

Conc. $H_2SO_4$ (80 mL) was added slowly to a stirred solution of 3,5-dihydroxybenzoic acid 301 (50 g, 0.33 mol) in $CH_3OH$ (660 mL) at rt and this solution was heated to reflux for 24 h. The reaction mixture was cooled to rt and $H_2O$ (500 mL) was added to the solution. The solution was extracted with EtOAc (3×300 mL), and the combined organic extracts were washed with a saturated aq $NaHCO_3$ solution (2×300 mL). The organic layer was dried ($Na_2SO_4$), and concentrated under reduced pressure to afford a white crude powder. The crude solid was purified by flush column chromatography (FCC) (10% ethyl acetate in hexane) to afford a white powdered ester 302 (48 g, 86%): $^1$H NMR (300 MHz, $CDCl_3$) δ 7.10 (2H, d, J=2.4 Hz HAr), 6.57 (1H, t, J=2.0 Hz, HAr), 4.99, (2H, br, s, HO), 3.84 (3H, s, $H_3COO$). The spectral data for 302 were in excellent accord with data previously reported on 302 (Seidel et al., 1990)[1]. This material was employed directly in the next step.

3,5-Dimethoxy Methylbenzoate (303)

The $(CH_3)_2SO_4$ (51.76 mL, 69 g, 0.547 mol) was added slowly to a stirred suspension of 302 (46 g, 0.27 mol) and anhydrous $K_2CO_3$ (94.45 g, 0.6835 mol) in acetone (700 mL) at rt and this mixture was heated to 50° C. and stirred for 48 h. Ice cold $H_2O$ (400 mL) was then added to the reaction mixture and the solution was extracted immediately with EtOAc (3×300 mL). The combined organic extracts were washed with brine (2×300 mL), dried ($Na_2SO_4$), and concentrated under reduced pressure to afford a yellow oil. The crude oil was purified by FCC (50% dichloromethane in hexane) to give a white powder 303 (92%), 303: $^1$H NMR (300 MHz, $CDCl_3$) δ 7.11 (2H, d, J=2.4 Hz HAr), 6.56 (1H, t, J=4.5 Hz, HAr), 3.91, (3H, s, $H_3COO$), 3.84 (6H, s, $H_3CO$). The spectral data for 303 were in excellent accord with data previously reported on this compound (Seidel et al., 1990)[1]. This material was employed directly in a later step.

3,5-Dimethoxy Benzylalcohol (304)

Ester 303 (25 g, 0.13 mol) in THF (50 mL) was added slowly to a dry stirred suspension of $LiAlH_4$ (7.25 g 0.19 mol) in THF (550 mL) at 0° C., The reaction mixture was stirred for 3 h at rt at which time all the starting material had disappeared (TLC). The reaction mixture was quenched by addition of ice-cold $H_2O$ (1.0 eq), 10% act NaOH (3.0 eq), and $H_2O$ (1.0 eq), sequentially and then filtered through a Buchner funnel. The filtrate was diluted with brine (800 mL) and extracted with EtOAc (3×300 mL). The combined organic extracts were dried ($Na_2SO_4$) and concentrated in vacuum. The crude oil was purified by FCC (20% ethylacetate in hexane) to afford a yellow oily alcohol 304 (17.5 g, 82%): $^1$H NMR (300 MHz, $CDCl_3$) δ 6.53 (2H, d, J=6.0 Hz HAr), 6.35 (1H, t, J=2.4 Hz, HAr), 4.49 (214, s, $H_2COH$), 3.80 (611, s, $H_3CO$). The spectral data for 304 were in excellent accord with data previously reported on it (Seidel et al., 1990)[1]. This material was employed directly in the next step.

3,5-Dimethoxy Benzylbromide (305)

Phosphorus tribromide (0.4 eq) was added to the alcohol 304 (25 g, 0.13 mol) in THF (100 mL) very slowly at −10° C. and the mixture which resulted was stirred for 15-30 min at the same temperature. By this time all the starting material had disappeared (TLC). The reaction mixture was quenched by addition of ice-cold $H_2O$ (100 mL) and then filtered through a Buchner funnel.

The filtrate was diluted with brine (100 mL) and extracted with EtOAc (3×300 mL). The combined organic extracts were dried ($Na_2SO_4$) and concentrated in vacuum. The crude oil was purified by FCC (20% ethylacetate in hexane) to afford the bromide 305 as a white solid (92%)[a]: $^1$HNMR (500 MHz, $CDCl_3$) δ 6.61 (2H, d, J=2.3 Hz), 6.46 (1H, t, J=2.3 Hz), 4.5 (2H, s), 3.85 (6H, s). $^{13}$C NMR (125 MHz, $CDCl_3$): δ 161.3, 140.2, 107.4, 101.0, 55.8, 34.1. The spectral data for 305 were in excellent accord with data previously reported on it (Seidel et al., 1990)[1]. This material was employed directly in the next step.

Synthesis of Diethylbenzylphosphonate (306) and its Conversion into the 3,5-dimethoxybenzothiostilbene (307)

Benzylbromide 305 (0.7 mL, 1.0 g, 5.85 mmol.) was heated with excess triethylphosphite (1.5 mL, 1.46 g, 8.76 mmol) at 130° C. under argon for 3 h while an outlet was set through the septum (16 guess needle) so that the volatile byproduct can be removed by evaporation during the reaction period. This gave phosphonate 306 (1.23 g, 92%), which was employed directly for the next step without any further purification[7].

Aldehyde 309 (1 g, 6.02 mmol) was added slowly to a combined solution of dry 3,5-dimethoxyethylbenzylphosphonate 306 (1.51 g, 6.62 mmol) and NaH (60% wt dispersed in mineral oil, 842 mg, 21.1 mmol) in dry DMF (5.0 mL), under argon at 0° C. This mixture was stirred at rt for 2 h, after which the reaction mixture was heated to 80-90° C. and stirred for an additional 1 h. The reaction solution was quenched by adding ice cold water slowly (25 mL) and extracted with EtOAc (50 mL×5). The total organic extract was washed with brine (100 mL×3), dried over $Na_2SO_4$ and evaporated on a rotatory evaporator. The crude solid which resulted was purified by FCC on silica gel (20% ethyl acetate in hexane) to afford pure 3,5-dimethoxybenzothiostilbene 307 (1.22 g, 85%), $^1$HNMR (300 MHz, $CDCl_3$) δ 7.82-7.71 (2H, m), 7.38-7.28 (411, m), 6.96 (1H, d, J=15.9 Hz), 6.70 (2H, d, J=2.2 Hz), 6.45 (1H, t, J=2.2 Hz), 3.87 (6H, s). $^{13}$C NMR (75 MHz, $CDCl_3$): δ 161.5, 143.2, 140.7, 139.1, 131.3, 125.3, 125.0, 124.0, 123.9, 123.3, 122.7, 105.1, 101.0, 55.9. HRMS (EI) (M)+, Calcd. for $C_{18}H_{16}O_2S$ 296.0871; Found 296.0864.

(E)-3-(2-(Benzo[b]thiophen-2-yl)vinyl)-5-methoxyphenol 8, (SK-03-92)

The NaH (60% dispersed in mineral oil, 3.6 g, 0.090 mol) was added to anhydrous DMF (100 mL) at 0° C., The $CH_3CH_2SH$ (12.2 mL, 13.22 g, and 0.12 mol) was then added dropwise and stirred at 0° C. for 30 min. The temperature of the reaction mixture was allowed to rise to rt and the mixture stirred for 1 h. Then the temperature of the reaction mixture was raised to 140° C. and at 140° C. the 3,5-dimethoxybenzothiostilbene 307 (5.0 g, 0.03 mol) in dry DMF (30 mL) was added dropwise to the reaction mixture. This mixture was held at 140° C. and stirred for 1 h at this temperature. The reaction mixture was then cooled to rt and quenched by addition of brine (540 mL). This was followed by addition of formaldehyde (37% aq. 42 mL) and HOAc (68 mL). This mixture was extracted with EtOAc (3×200 mL). The combined organic layers were washed sequentially with a saturated aq solution of $NH_4Cl$ (3×60 mL), and with brine (3×60 mL). The organic layer was dried ($Na_2SO_4$), and the solvent was removed in vacuum. The crude oil was purified by FCC (20% ethylacetate in hexane) to afford the desired 3-hydroxy-5-methoxybenzothiostilbene 308 (92%) as a pale yellow solid: $^1$HNMR (300 MHz, $CD_3COCD_3$): δ 8.43 (1H, s), 7.89-7.77 (2H, m), 7.52-7.34 (4H, m), 6.97 (1H, d, J=15.9 Hz), 6.72 (2H, m), 6.40 (1H, t, J=2.2 Hz), 3.81 (3H, s). $^{13}$C NMR (75 MHz, $CD_3COCD_3$): δ 161.3, 158.7, 142.7, 140.3, 138.6, 130.8, 124.8, 124.5, 123.6, 123.4, 122.4, 122.0, 106.2, 103.4, 101.5, 54.6. HRMS (EI) (M)+, Calcd. for $C_{17}H_{14}O_2S$ 282.0715; Found 282.0722. Anal. Calcd for $C_{17}H_{14}O_2S$ (MW: 282.36 g/mol): C, 72.31; H, 5.00; O, 11.33; S, 11.36. Found: C, 72.07; H, 4.99. Log P: 7.47; C log P: 5.2962.

APPENDIX

The information contained in the attached Appendix is expressly incorporated by reference herein in its entirety.

REFERENCES WHICH ARE EXPRESSLY INCORPORATED BY REFERENCE HEREIN IN THEIR ENTIRETY

1. Asianscientist: http://www.asianscientist.com/features/skin-whitening-products-asia-2012/
2. Choi, T-Y., Kim, J-H., Ko, D. H., Kim, C-H., Hwang, J-S., Ahn, S., Kim, S. Y., Kim, C-D., Lee, J H., and Yoon, T-J. (2007). Zebrafish as a new model for phenotype-based screening for melanogenic regulatory compounds. Pigment Cell Res. 20; 120-127.
3. Kanebo (2013): http://www.kanebo.com/pressroom/pressrelease/20130723.pdf
4. Kabir, M. S., Engelbrecht, K., Polanowski, R., Rott, M. A., Schwan, W. R., Stemper, M., Reed, K., Sherman, D., Cook, J. M., Monte, A., (2008). New class of gram-positive antibacterials: Inhibitors of MRSA and surrogates of the causative agents of anthrax and tuberculosis. Bioorg. Med. Chem. Lett. 18: 5745-5749.
5. Rodriguez, R., Haugen, R., Rueber, A., and Huang, C-C. (2014). Reversible neuronal and muscular toxicity of caffeine in developing vertebrates. Comp. Biochem. Physiol. Part C (in press).
6. Smit, N., Vicanova, J., and Pavel, S. (2009). The hunt for natural skin whitening agents. Int. J. Mol. Sci. 10:5326-5349.

Various other embodiments of the present invention are contemplated as being within the scope of the filed claims particularly pointing out and distinctly claiming the subject matter regarded as the invention.

The invention claimed is:

1. A cancerous cell growth inhibiting compound having the following formula:

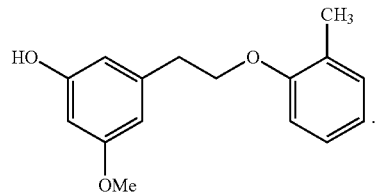 [SMILES: COc1cc(O)cc(CCOc2ccccc2C)c1]

2. A method of inhibiting cancerous cell growth, said method comprising the step of administering an effective amount of a compound having the following structure:

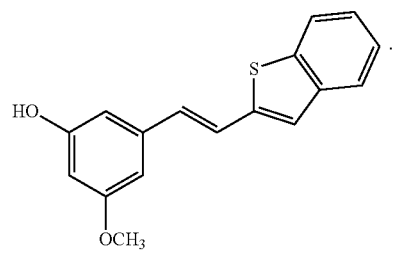 [SMILES: COc1cc(O)cc(/C=C/c2cc3ccccc3s2)c1]

* * * * *